(12) United States Patent
Ben-Oren et al.

(10) Patent No.: US 7,063,667 B1
(45) Date of Patent: Jun. 20, 2006

(54) ISOTOPIC GAS ANALYZER

(75) Inventors: Ilan Ben-Oren, Jerusalem (IL); Lewis Colman, Jerusalem (IL); Ephraim Carlebach, Raanana (IL); Boaz Giron, Jerusalem (IL); Gershon Levitsky, Jerusalem (IL)

(73) Assignee: Oridion BreathID Ltd., Jerusalem (IL)

( * ) Notice: Subject to any disclaimer, the term of this patent is extended or adjusted under 35 U.S.C. 154(b) by 0 days.

(21) Appl. No.: 09/508,805

(22) PCT Filed: Sep. 17, 1998

(86) PCT No.: PCT/IL98/00458

§ 371 (c)(1),
(2), (4) Date: May 31, 2000

(87) PCT Pub. No.: WO99/14576

PCT Pub. Date: Mar. 25, 1999

(30) Foreign Application Priority Data

Sep. 17, 1997  (IL) .................................... 121793

(51) Int. Cl.
*A61B 5/00* (2006.01)

(52) U.S. Cl. .......................... 600/532; 73/23.3; 422/84

(58) Field of Classification Search ............... 600/532, 600/32–324; 73/23.2, 23.21, 23.3; 422/83, 422/84; 42/84
See application file for complete search history.

(56) References Cited

U.S. PATENT DOCUMENTS

| | | | |
|---|---|---|---|
| 3,830,630 A * | 8/1974 | Kiefer et al. ............... 436/132 |
| 4,578,762 A | 3/1986 | Wong |
| 4,684,805 A | 8/1987 | Shu-Ti Lee ................. 250/343 |
| 4,723,435 A | 2/1988 | Huszczuk |
| 4,755,675 A | 7/1988 | Rosenfeld .................... 250/343 |
| 5,046,491 A | 9/1991 | Derrick et al. |
| 5,050,615 A | 9/1991 | Malkamaeki et al. |
| 5,127,406 A * | 7/1992 | Yamaguchi ................. 600/322 |
| 5,140,993 A | 8/1992 | Opekun, Jr. et al. ........ 128/730 |
| 5,146,294 A | 9/1992 | Grisar et al. ................ 356/435 |
| 5,239,492 A | 8/1993 | Hartwig et al. |
| 5,300,859 A | 4/1994 | Yatsiv ......................... 313/573 |
| 5,303,575 A | 4/1994 | Brown et al. |
| 5,317,156 A * | 5/1994 | Cooper et al. .............. 250/345 |
| 5,335,656 A | 8/1994 | Bowe ..................... 128/207.18 |
| 5,394,236 A * | 2/1995 | Murnick ..................... 356/311 |
| 5,479,019 A * | 12/1995 | Gross ......................... 250/345 |
| 5,486,699 A | 1/1996 | Fabinski et al. ............ 250/345 |
| 5,543,621 A | 8/1996 | Sauke et al. |
| 5,553,177 A | 9/1996 | Hering et al. ................. 385/31 |
| 5,640,014 A | 6/1997 | Sauke .................... 250/339.03 |
| 5,747,809 A * | 5/1998 | Eckstrom .................... 250/345 |
| 5,908,789 A * | 6/1999 | Weeckstrom ................ 422/84 |
| 5,929,442 A * | 7/1999 | Higashi ................. 250/339.13 |
| 5,957,858 A * | 9/1999 | Micheels et al. ........... 600/532 |
| 5,964,712 A * | 10/1999 | Kubo et al. ............. 600/532 |
| 6,234,001 B1 | 5/2001 | Sorensen et al. |

FOREIGN PATENT DOCUMENTS

| | | |
|---|---|---|
| DE | 44 02 054 A | 7/1995 |
| DE | 297 06 668 U | 6/1997 |
| EP | 0 551 142 | 7/1993 |
| EP | 0 584 897 A1 | 3/1994 |
| EP | 0 661 583 | 7/1995 |
| GB | 2 324 387 | 10/1998 |
| WO | WO 93/15391 | 8/1993 |
| WO | WO 97/14029 | 4/1997 |
| WO | WO 98/30888 | 7/1998 |

OTHER PUBLICATIONS

M. Haisch, "Quantitative Isotope-Selective Infra-red Spectroscopy for Determining the Isotopic Ratio Carbon Dioxide in Breath", Heinrich-Heine University, Dusseldorf, 1995, XP002041167.

D.A. Schoeller et al., "$^{13}$C Abundances of Nutrients and the Effect of Variations in $^{13}$C Isotopic Abundances of Test Meals Formulated for $^{13}CO_2$ Breath Tests", *The American Journal of Clinical Nutrition*, 35, Nov. 1980, pp. 2375-2385.

R.R. Wolfe, *Tracers in Metabolic Research—Radio Isotopes and Stable Isotope/Mass Spectrometer Methods*, Chap. 16, Alan R. Liss, Inc., New York, 1984.

Iris® —Infra Red Isotope Analyser, Wagner Analysen Technik, Vertriebs—GmbH.

* cited by examiner

*Primary Examiner*—Robert L. Nasser
(74) *Attorney, Agent, or Firm*—Amster, Rothstein & Ebenstein LLP

(57) ABSTRACT

An NDIR spectrometer based on the use of wavelength specific lamp sources, whose emission spectrum consists of discrete, narrow lines characteristic of the isotope present in the lamp, and which it is desired to measure with the spectrometer. This allows very high intrinsic sensitivity, enabling the use of an extremely compact absorption cell with a very short path length. In addition, the source can be self-modulated, such that problems associated with external choppers are avoided. Furthermore, there is insignificant cross sensitivity between the isotopes themselves and between the isotopes and other ambient gases in the operating environment.

69 Claims, 29 Drawing Sheets

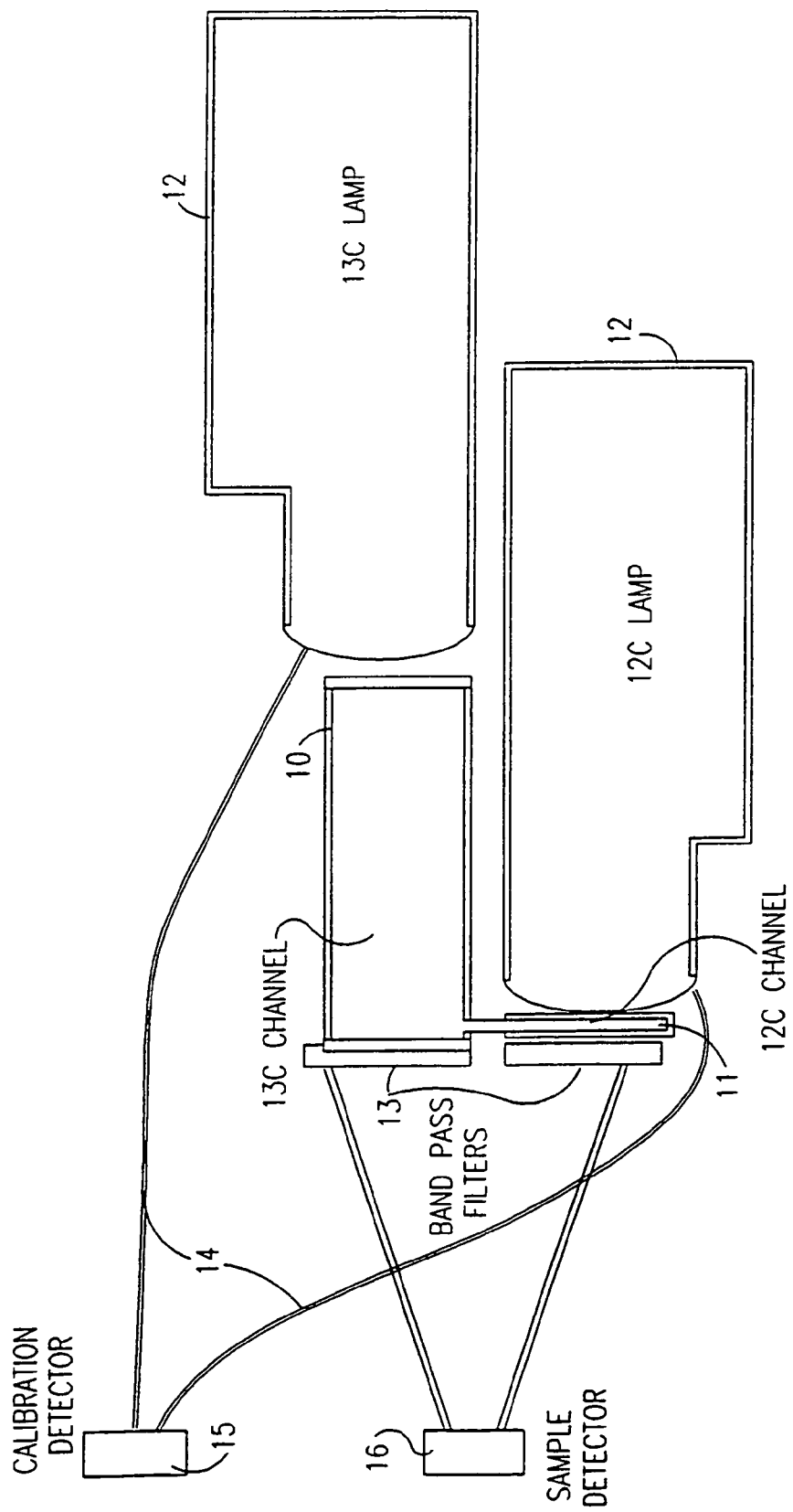

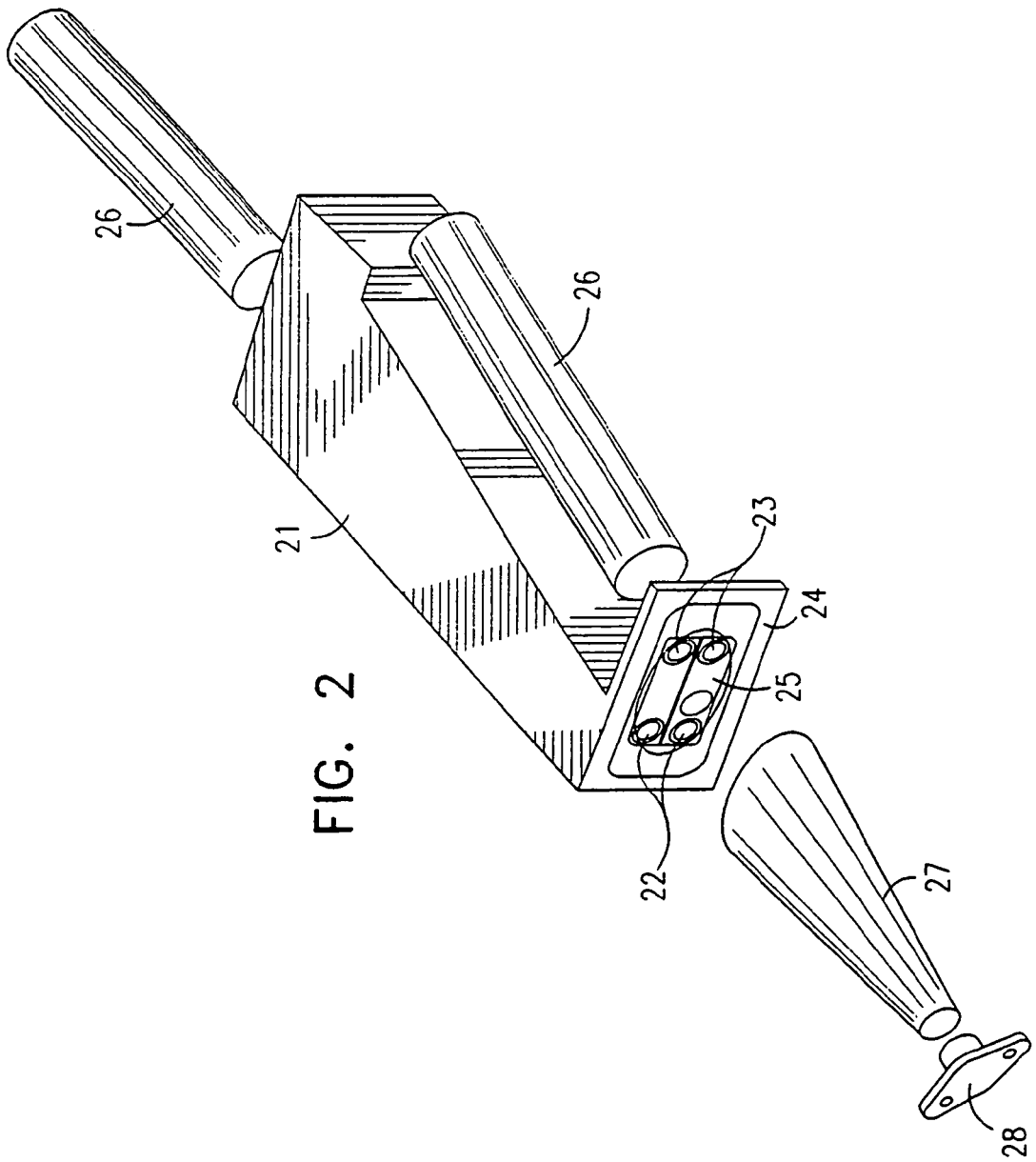

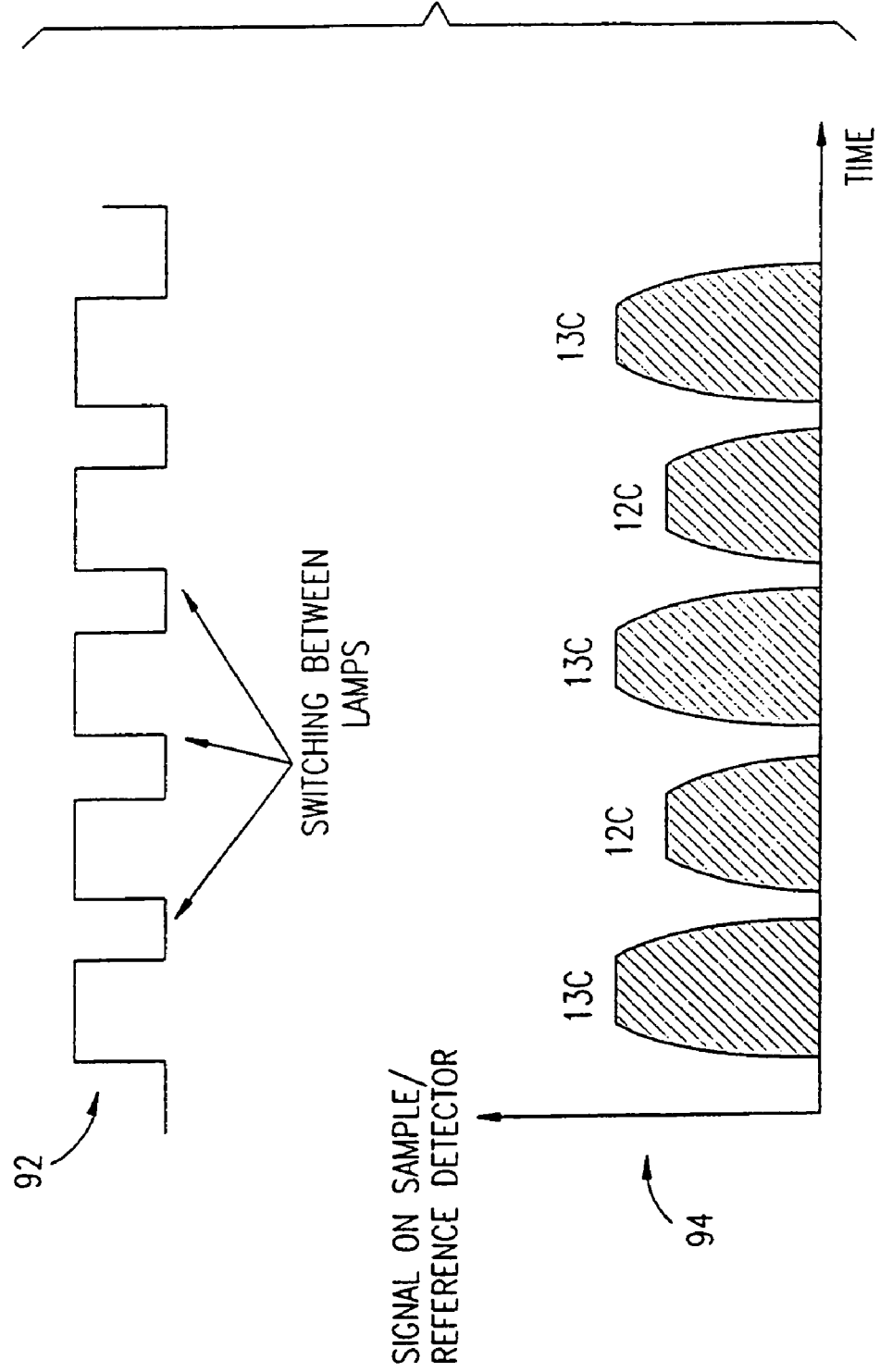

FIG. 10A
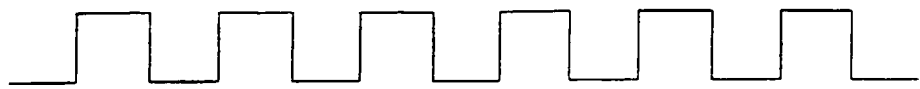
FIG. 10B
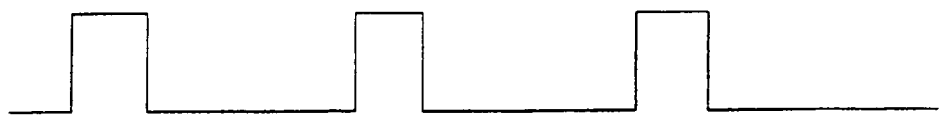
FIG. 10C
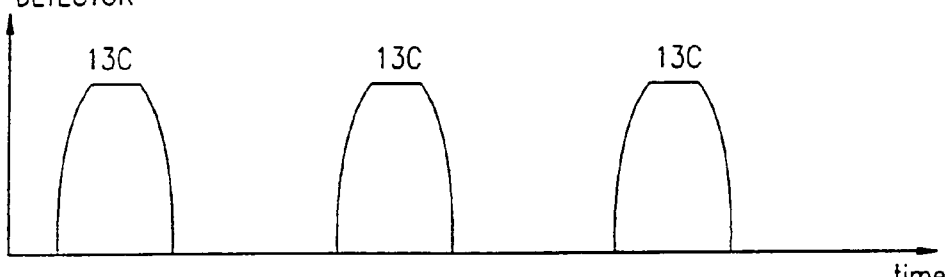
FIG. 10D
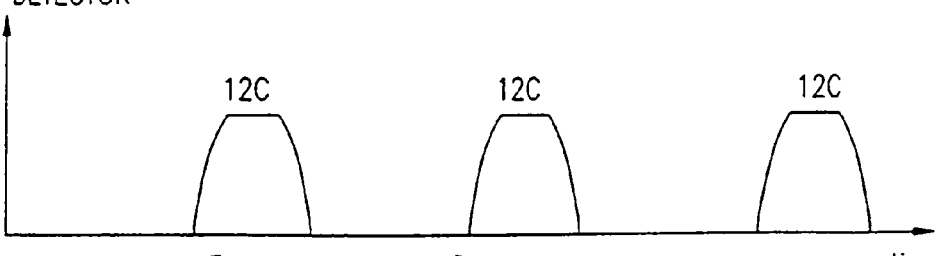
FIG. 10E

ISOTOPIC GAS ANALYZER

FIELD OF THE INVENTION

This invention relates to the field of analyzers for determining the isotopic ratio of gases, especially in exhaled breath.

BACKGROUND OF THE INVENTION

A commonly use method of measuring the isotopic ratio of components of a gaseous sample is that of comparing the gaseous sample in a measurement cell, with a reference gas measured under similar conditions. Such a method, using mass spectrometric measurements as the comparison criterion, has been described in Chapter 16 of the book entitled "Tracers in Metabolic Research—Radio-isotopes and Stable Isotope/Mass Spectrometer Methods" by Robert R. Wolfe, Alan R. Liss Inc., New York (1984). The disclosures of that publication and of all other publications mentioned in this specification, and the disclosures of all documents cited in those publications, are hereby incorporated by reference.

Infra-red gas absorption can also be used as a means of analyzing the content of gaseous mixtures, since each gas has its own absorption characteristics, which differentiates it from other gases. The non-dispersive absorption of light in a gas is governed by the well-known Lambert-Beer law, which states that:

$$I = I_o \cdot \exp\{-[c] \cdot \Upsilon \cdot d\}$$

where I is the intensity of the transmitted light, $I_o$ is the intensity of the incident light,

[c] is the molar concentration of the gas absorbing the light, d is the path length of the light in the gas, and $\Upsilon$ is the absorption coefficient per unit length, also known as the extinction coefficient.

The molar concentration of the gas is directly proportional to its partial pressure, for a given volume of gas at a given temperature. It would therefore seem that a simple measurement of the transmission of light through a known length of the gas to be analyzed would be sufficient to determine its partial pressure or concentration. This is the basis of the technique known as non-dispersive infra-red spectroscopy, which is a primary methods in use today for gas analysis, and a large volume of reference work is available on the subject. Isotopic differentiation is becoming an increasingly important analytical tool, especially in such fields as breath tests for medical diagnostic testing. Sensitive NDIR spectrometers, capable of measuring changes in rare isotopic concentrations, are thus becoming important in the field of medical instrumentation, and others.

The absorption phenomenon used for performing such NDIR spectroscopy, as it is known, is the absorption of light energy by gaseous molecules undergoing transitions between rotational-vibrational levels. The energy levels involved place these transitions in the infra-red region of the spectra. As an example, the absorption spectra of $CO_2$ molecules is centered in the 4.2 to 4.45 μm region, and in general, black body infra-red sources have been used for performing such measurements. Such black body sourced spectrometers have difficulty in differentiating between various isotopes of gases, since there is only an extremely small shift in absorbed wavelength when an atom in a gas is replaced by a chemically identical isotopic atom. Since isotopic differentiation is becoming an increasingly important analytical tool, especially in such fields as breath tests in medical diagnostic testing, sensitive NDIR spectrometers capable of measuring changes in rare isotopic concentrations, are becoming important in the field of medical instrumentation and others.

In order to define the exact wavelength of the measurement, a means for discriminating between the various isotopes of the gas sample is needed. If a black body is used as the source of radiation, it is necessary to use some form of sophisticated narrow band filter, which would transmit only those regions where no spectral overlap is possible. Because of the inherent continuous nature of the black body spectrum, as opposed to the discrete nature of the absorption spectrum of the isotopic gas mixture, by using only those remaining spectral regions makes this method insensitive for isotope discrimination, and requires the use of very long optical absorption paths to achieve adequate sensitivity. In addition, black bodies cannot be modulated at frequencies which give useful detection advantages and so have to have modulation applied to their radiation by external means.

Even if a wavelength sensitive detector, such as an acousto-optic detector, is used with the black body to define a narrow wavelength region where the absorption measurement takes place, significant overlap of the various isotope spectral absorption lines dictates the use of complex correction and compensation algorithms, as shown for instance in European Patent Application No. EP 0 584 897 A1 to W. Fabinsky et al.

As an alternative technology, in U.S. Pat. No. 4,755,675 there is described a gas analyzer using a wavelength specific infra-red lamp source, based on a gas-filled discharge tube, which emits the characteristic spectral lines of the gas filling the lamp. By selecting the filling gas, it is possible to perform analysis of gas mixtures containing the gas used for the lamp fill. The authors even suggest that, being able to make use of such specific IR sources, an IR analyzer according to their invention would be capable of identifying and measuring the concentration of isotopically substituted "marker" molecules. However, the patent does not provide any explanation of how this can be performed in practice. These lamps have been successfully used in capnography applications. However, for use in gas isotopic measurements, which require sensitivity and selectivity at least one order of magnitude higher than for capnographic measurements, the measurement and application techniques previously reported are totally inadequate.

Part of the complexity of gas isotope analysis arises because the Lambert-Beer law is only an approximation. In particular, the absorption coefficient $\Upsilon$, is not a constant at all, but is dependent on a wide range of environmental factors, such as the analyzed gas pressure and temperature, the ambient humidity, the spectral characteristics resulting from the operating conditions of the radiating source, gas carriers in the analyzed gas, and short and long term changes in the radiating source spectral characteristics. Many of the NDIR spectrometers described in the prior art have attempted to overcome this problem by using closely controlled environmental conditions, predetermined correction factors, or frequent, complex calibration techniques, or a combination of all three. Some examples of such prior art analyzers include the analyzer described by W. Fabinsky et al. in European Patent No. EP 0 584 897 A1, that described by R. Grisar et al. in U.S. Pat. No. 5,146,294, and that described by Y. Kubo et al. in PCT Patent Application No. WO 97/14029.

In U.S. Pat. No. 5,140,993, to A. R. Opekun and P. D. Klein, is described a device for collecting a breath sample. This breath sample collection bag is operative to collect breaths exhaled by a patient, until sufficient have been collected for transfer to the analysis instrument. The breaths are inputted into the bag by means of a mouthpiece into which the patient blows, and the entry of the breath is controlled either by a check valve, that permits gas flow only towards the inside of the bag, or by a stop-cock valve, manually operated either by the patient himself or by an attending medical assistant. No criteria are given for the opening of the check valve, other than its function to permit gas flow only towards the inside of the bag, as for the stop-cock valve. This breath sample collection bag thus acts as a very simple form of collection reservoir, performing simple breath averaging, with the limited advantages which this offers.

To the best of applicants' knowledge, none of the prior art instruments attach importance to the fact that if parts of the breath other than from the plateau are collected for analysis, there may be serious implications for the measurement accuracy.

All of the above described prior art analyzers appear to be complex, costly analytical instruments, which in most cases are also difficult to operate because of the rigorous and frequent calibration procedures required. To the best of the inventors' knowledge, no prior art gas analyzers exist which provide sufficient sensitivity and selectivity that enable them to be used for tests such as medical isotopic breath testing, and yet which are sufficiently compact, rugged and low cost, not requiring stable laboratory environments to enable them to become accepted for widespread use in the medical community.

The disclosures of all publications mentioned in this section and in the other sections of the specification, and the disclosures of all documents cited in the above publications, are hereby incorporated by reference.

SUMMARY OF THE INVENTION

The present invention seeks to provide an apparatus for analyzing the ratio of isotopic gases in a mixture containing two or more of such isotopes, which overcomes the drawbacks and disadvantages of prior art analyzers, and in particular, which provides analytic instrument performance standards in a compact, rugged and low cost instrument, operative outside the laboratory environment.

There is thus provided in accordance with a preferred embodiment of the present invention, an NDIR spectrometer based on the use of wavelength specific lamp sources, whose emission spectrum consists of discrete, narrow lines characteristic of the isotope present in the lamp, and which it is desired to measure with the spectrometer. This allows very high intrinsic sensitivity, enabling the use of an extremely compact absorption cell with a very short path length. In addition, the source can be self-modulated, such that problems associated with external choppers are avoided. Furthermore, there is insignificant cross sensitivity between the isotopes themselves, and between the isotopes and other ambient gases in the operating environment, such as $N_2O$, whose absorption spectrum overlaps that of $^{13}CO_2$.

In order to overcome the serious problem of thermal drift in infra-red detectors, for example, in PbSe detectors, typically 2% to 4% per degree C, a cross detection scheme is used in the present invention whereby each detector detects signals from more than one isotopic absorption channel. Thermal drift thus affects each channel equally. Furthermore, since the present invention measures the isotopic ratio, and not the absolute absorption values, any such residual thermal drift effect becomes of second order importance only. This cross detection scheme is not feasible with wavelength specific detectors, such as acousto-optical detectors, since each detector is specific to one wavelength, and hence can only detect the isotope it was intended to detect.

In addition, in order to reduce sensitivity to environmental changes, and to allow compact, rugged and low cost construction, and reliable and simple operation, with minimal infrequent calibration procedures, the NDIR spectrometer is constructed and operative with the reference and sample channels in close thermal and physical contact, and with gas fills of closely matched partial pressures of the isotopes of interest, such that both are affected in a similar manner by changes in environmental conditions. The reference gas channel therefore fully follows the physical, electronic and environmental changes which occur in the whole system and accurately tracks changes in absorption due to these factors in the sample gas.

Moreover, the cell length, radiation sources, and filters are chosen such that the absorption curves of the $^{12}CO_2$ and the $^{13}CO$ in their respective channels are very close, so that errors and changes in the source intensities generate the same errors in the $^{12}CO_2$ and the $^{13}CO_2$ concentration measurements, which therefore cancel out in the ratio measurement.

Furthermore, the signal detection and processing scheme is designed to extract the maximum resolution and accuracy in a ratio measurement of the isotopes, rather than in an absolute measurement. The electro-optical system is such that wherever possible, sources of drift in individual parallel components are eliminated by using single components operative for performing multiple functions. This is apparent in the various embodiments whereby a single detector with signal encoding is used to monitor more than one channel, or a single lamp is used to emit spectral lines from more than one isotope.

The present invention also seeks to provide a novel intermediate chamber arrangement for collecting and selectively handling multiple samples of the gas to be analyzed, before passing the gas on to the analyzer chamber itself. The intermediate chamber according to the present invention, can be used both for mass spectrometric gas analyzers and for those based on non-dispersive infra-red absorption spectrometers.

The intermediate chamber according to the present invention, by means of its gas handling system, selectively collects part or all of multiple samples of the gas to be analyzed. In the simplest embodiment of the present invention, all of the plateaus of the collected samples are used, and in this way, only exhaled breath which has a direct correlation to the blood gas level is collected. According to more advanced embodiments, the gas handling system discards part of the collected samples, or dilutes the accumulated sample until a predefined partial pressure of the major isotopic gas is obtained. The accumulated sample is then transferred to the analyzing chamber for measurement. In this way, the analyzer is provided with a series of samples to be measured, with the closest possible concentration of the major isotopic gas between sample and sample.

Though the intermediate chamber according to the present invention is applicable to analysis systems for isotopic ratios in any gaseous mixture, it is described in the main in this patent application in terms of one of the most common applications, namely that used in breath test apparatus for the detection of the isotopic ratio of $^{13}CO_2$ to $^{12}CO_2$ in a patient's breath. In the more advanced embodiments of this application, the aim of the intermediate chamber system is to ensure that the $^{12}CO_2$ concentrations of successive samples passed to the analyzer from the intermediate chamber should have as close concentrations to one another, as possible. This mode of operation provides a number of advantages which increase the accuracy of the isotopic ratio measurement, as follows:

a) If all of the measurement points are in the same concentration area, then the effect of changes in the curve of the optical transmission of the gas in the sample chamber, as a function of its concentration (hereinafter, the "absorption curve"), is minimized.

b) There is less cross-sensitivity (the effect of $^{12}CO_2$ concentration on the $^{13}CO_2$ measurement).

c) In some measurement schemes, a reference gas with a constant and known $^{12}CO_2$ concentration is used. If the measured gas has a concentration very close to that of the reference gas, the accuracy of the measurement is increased since the anchor point of the absorption curve is defined close to the measurement point.

d) The system is optimized in terms of the length of the optical absorption cell, to give optimum sensitivity and minimum dependence of sensitivity on gas concentration.

The intermediate chamber system according to the present invention has some additional side benefits, not directly related to the improved accuracy afforded by its use, namely:

e) Nasal cannula can be used for collecting relatively small amounts of exhaled breath without involvement of the patient whose breath is being tested.

f) The breath of infants can also be tested since a large number of breaths can be accumulated for each measurement cycle.

g) The intermediate chamber can be used to perform a self calibration procedure.

h) Pneumatic preconditioning of the sample is possible, as mentioned above. This preconditioning is dynamically controlled as a function of the constitution of the exhaled breath, by means of a fast capnographic probe in the breath collection line, for determining the temporally changing content of each exhaled breath sample. In this way, any part or parts of the breath wave can be selected for accumulation in the intermediate chamber.

According to a preferred embodiment of the present invention, iterative integration of successive breath samples is performed until the main isotope concentration of the accumulated gas in the intermediate chamber has a specific predefined level, typically of the order of 3 to 4%. The accumulated gas is transferred for measurement to the analysis chamber only when this predefined level has been reached after a specific volume of sample gas has been accumulated. The intermediate chamber system is even able to dilute the accumulated gas, if necessary, by the use of a switched gas absorber unit in the sample inlet line, such as a $CO_2$ scrubber in the case of the $CO_2$ breath test implementation. By all of these means, the intermediate chamber system ensures that the main isotope concentrations of individual transferred samples, are maintained at very close levels, typically better than ±0.2%.

The advantages of this method over that of Grisar et al. as mentioned above in U.S. Pat. No. 5,146,294, are thus obvious. In the Grisar method, the object is to obtaining the highest $CO_2$ concentration possible, and then to dilute it down with a neutral gas. This method has a number of drawbacks, namely: (i) It is time consuming (ii) It is very complex (iii) The system is expensive to construct (iv) It does not enable the concentration to attain very exact values. In the intermediate chamber according to the present invention, iterative integration of breaths is performed dynamically during the whole of the collection process, aiming at a predefined target concentration right from the very first breath. The whole process is performed (i) in real time (ii) the system consists of a simple pneumatic circuit, without any connection to external gas supplies (iii) the target concentration levels obtained are very accurate (iv) the system collects an accurately selected part of the plateau for optimum physiological correlation with the patient's clinical condition.

Furthermore, the Grisar method is based on the use of a formula for calculating the isotope ratio, which is only valid if the partial pressures of $^{12}CO_2$ in the measuring cell and the reference cell are identical, which makes the estimation of the $^{13}CO_2$ concentration simple. In the present invention, there is no need for this exact partial pressure matching. Only an approximate match is needed, and that not in order to perform the measurement itself accurately, but rather in order to reduce the effect of environmental inaccuracies.

The use of the intermediate chamber system in accordance with the present invention also enables a number of self-calibration features to be incorporated. Firstly, the intermediate chamber system itself can be self-calibrated against the results of the isotopic ratio test performed by the gas analyzer. In addition, the same self-test can be extended by utilizing a single high concentration sample of breath from a healthy subject, and diluting it using the intermediate chamber system to obtain a number of additional calibration check points. Finally, this self-check can be performed, according to the present invention, on a continuous background basis on multiple negative samples of healthy subjects, even on gas analyzers which do not incorporate intermediate chamber systems.

There is therefore provided in accordance with a preferred embodiment of the present invention, an isotopic gas analyzer including an optical absorption analyzer for analyzing at least one isotope in a sample gas, the optical absorption analyzer including at least one wavelength-stable source of radiation which is specific to the at least one isotope.

There is further provided in accordance with a preferred embodiment of the present invention, an isotopic gas analyzer as described above and wherein the wavelength-stable source is a gas discharge source.

There is further provided in accordance with a preferred embodiment of the present invention, an isotopic gas analyzer as described above and wherein the analyzer determines the ratio of at least two isotopes in the sample gas.

There is further provided in accordance with a preferred embodiment of the present invention, an isotopic gas analyzer as described above and wherein the at least one wavelength-stable source of radiation comprises at least two wavelength-stable sources of radiation, each being specific to at least one isotope.

There is further provided in accordance with a preferred embodiment of the present invention, an isotopic gas analyzer as described above and wherein the at least one wavelength-stable source of radiation which is specific to at least one isotope is specific to two isotopes.

There is further provided in accordance with a preferred embodiment of the present invention, an isotopic gas analyzer including an optical absorption analyzer for analyzing the ratio of at least two isotopes in a sample gas, the optical absorption analyzer including at least one wavelength-stable source of radiation which is specific to the at least one isotope.

There is further provided in accordance with a preferred embodiment of the present invention, an isotopic gas analyzer including an optical absorption analyzer for analyzing at least one isotope in a sample gas, the optical absorption analyzer including two wavelength-stable sources of radiation, each of which is specific to at least one isotope.

There is further provided in accordance with a preferred embodiment of the present invention, an isotopic gas analyzer including an optical absorption analyzer for analyzing at least one isotope in a sample gas, the optical absorption analyzer including at least one wavelength-stable source of radiation which is specific to two isotopes.

There is further provided in accordance with a preferred embodiment of the present invention, an isotopic gas analyzer as described above and wherein the optical absorption analyzer includes a reference gas channel, and wherein the sample gas is maintained under the same conditions as the reference gas.

There is further provided in accordance with a preferred embodiment of the present invention, an isotopic gas analyzer as described above and wherein the reference channel gas is a sample of the sample gas.

There is further provided in accordance with a preferred embodiment of the present invention, an isotopic gas analyzer as described above and wherein the reference channel gas is a mixture containing the at least one isotope at a known pressure and concentration.

There is further provided in accordance with a preferred embodiment of the present invention, an isotopic gas analyzer as described above and wherein the spectral overlap area is utilized by lowering the gas pressures.

There is further provided in accordance with a preferred embodiment of the present invention, an isotopic gas analyzer including at least first and second gas discharge lamps operated with respective first and second different timing characteristic least one detector viewing outputs of the at least first and second gas discharge lamps in the presence of gas to be analyzed, and a detection differentiator receiving an output from the at least one detector and distinguishing outputs corresponding to the first and second gas discharge lamps on the basis of the first and second different timing characteristics.

There is further provided in accordance with a preferred embodiment of the present invention, an isotopic gas analyzer as described above and wherein the first and second different timing characteristics are first and second frequencies.

There is further provided in accordance with a preferred embodiment of the present invention, an isotopic gas analyzer as described above and wherein the first and second different timing characteristics are first and second phases.

There is further provided in accordance with a preferred embodiment of the present invention, an isotopic gas analyzer as described above and wherein the at least one detector viewing outputs of the at least first and second gas discharge lamps in the presence of gas to be analyzed is a single detector.

There is further provided in accordance with a preferred embodiment of the present invention, an isotopic gas analyzer as described above and wherein the at least one detector viewing outputs of the at least first and second gas discharge lamps in the presence of gas to be analyzed are two detectors, each viewing one of first and second gas discharge lamps.

There is further provided in accordance with a preferred embodiment of the present invention, an isotopic gas analyzer as described above and wherein the at least one detector viewing outputs of the at least first and second gas discharge lamps in the presence of gas to be analyzed are two detectors, one viewing absorption signal outputs from first and second gas discharge lamps and one viewing zero calibration from first and second gas discharge lamps.

There is further provided in accordance with a preferred embodiment of the present invention, an isotopic gas analyzer as described above and wherein the detection differentiator receiving an output from the at least one detector and distinguishing outputs corresponding to the first and second gas discharge lamps on the basis of the first and second different timing characteristics comprises first and second synchronized signal processors, such as lock-in amplifiers.

There is therefore provided in accordance with a preferred embodiment of the present invention, an isotopic gas analyzer including a discharge lamp containing at least first and second isotope labeled excitation gases, at least one detector viewing an output of the discharge lamp in the presence of gas to be analyzed, at least first and second filters corresponding to parts of respective first and second spectra of the at least first and second isotope labeled excitation gases, and a detection differentiator cooperating with the detector for distinguishing detector outputs corresponding to the at least first and second spectra.

There is further provided in accordance with a preferred embodiment of the present invention, an isotopic gas analyzer as described above and wherein the detection differentiator comprises at least one light valve modulating at least one of said light outputs of the first and second filters in accordance with a known timing sequence.

There is further provided in accordance with a preferred embodiment of the present invention, an isotopic gas analyzer as described above and wherein the at least one light valve modulating at least one of said light outputs of the at least first and second filters in accordance with a known timing sequence is a chopper.

There is further provided in accordance with a preferred embodiment of the present invention, an isotopic gas analyzer as described above and wherein the at least one light valve modulating at least one of said light outputs of the at least first and second filters in accordance with a known timing sequence is a spatial light modulator.

There is further provided in accordance with a preferred embodiment of the present invention, an isotopic gas analyzer as described above and wherein the at least one light valve is operated with respective first and second different timing characteristics and wherein the detection differentiator also comprises a detector output discriminator receiving an output from the detector and distinguishing outputs corresponding to the first and second excitation gases on the basis of the first and second different timing characteristics.

There is further provided in accordance with a preferred embodiment of the present invention, an isotopic gas analyzer as described above and wherein the first and second different timing characteristics are first and second frequencies.

There is further provided in accordance with a preferred embodiment of the present invention, an isotopic gas analyzer as described above and wherein the first and second different timing characteristics are first and second phases.

There is further provided in accordance with a preferred embodiment of the present invention, an isotopic gas analyzer as described above and wherein the detection differentiator comprises first and second synchronized signal processors.

There is therefore provided in accordance with a preferred embodiment of the present invention, an isotopic gas analyzer including a discharge lamp containing first and second isotope labeled excitation gases, first and second detectors each viewing an output of the discharge lamp in the presence of gas to be analyzed, and first and second filters, each corresponding to a part of respective first and second spectra of the first and second isotope labeled excitation gases interposed between the discharge lamp and respective ones of the first and second detectors.

There is further provided in accordance with a preferred embodiment of the present invention, an isotopic gas analyzer as described above and wherein the filters are at least one of optical or gaseous filters.

There is therefore provided in accordance with a preferred embodiment of the present invention, an isotopic gas analyzer including at least one gas discharge lamp containing at least first and second isotope labeled excitation gases having overlapping spectral ranges including at least some interdigitated spectral lines, a detector viewing outputs of the at least one gas discharge lamp in the presence of gas to be analyzed, and gas contents indicator receiving an output from the detector and employing information detected by the detector from at least two of the at least some interdigitated spectral lines.

There is further provided in accordance with a preferred embodiment of the present invention, an isotopic gas analyzer as described above and wherein the gas to be analyzed is maintained at a pressure below atmospheric pressure There is further provided in accordance with a preferred embodiment of the present invention, an isotopic gas analyzer as described above and wherein filters are used to isolate non overlapping spectral ranges including at least some interdigitated spectral lines;

There is therefore provided in accordance with a preferred embodiment of the present invention, an isotopic gas analyzer including an optical absorption analyzer for analyzing at least one isotope in a sample gas, the optical absorption analyzer including at least one wavelength-stable source of radiation which is specific to the at least one isotope, a channel containing a reference gas, and osmotic means for achieving substantially the same partial pressure of the main isotope of interest in the sample gas and the reference gas chambers.

There is therefore provided in accordance with a preferred embodiment of the present invention, an isotopic gas analyzer including an optical absorption analyzer for analyzing at least one isotope in a sample gas, the optical absorption analyzer including at least one wavelength-stable source of radiation which is specific to the at least one isotope, a channel containing a reference gas, and pumping means for achieving substantially the same concentration of the main isotope of interest in the sample gas and the reference gas chambers.

There is further provided in accordance with a preferred embodiment of the present invention, an isotopic gas analyzer as described above and wherein the absorption of the common isotope in the reference and sample channels are made substantially equal by means of a change in the length of at least one of the channels.

There is further provided in accordance with a preferred embodiment of the present invention, an isotopic gas analyzer as described above and wherein the gas analyzed is exhaled breath.

There is further provided in accordance with a preferred embodiment of the present invention, an isotopic gas analyzer as described above and wherein only a selected part of the exhaled breath is used for the analyzing.

There is further provided in accordance with a preferred embodiment of the present invention, an isotopic gas analyzer as described above and wherein an intermediate chamber is used to collect a plurality of breaths from at least part of the exhaled breath, and pumping means used for passing into analyzer.

There is further provided in accordance with a preferred embodiment of the present invention, an isotopic gas analyzer as described above and wherein the intermediate chamber has means to reduce its volume to drive out contents while maintaining substantially constant pressure.

There is further provided in accordance with a preferred embodiment of the present invention, an isotopic gas analyzer as described above and wherein the exhaled breath is continuously sampled by means of a connecting nasal cannula.

There is further provided in accordance with a preferred embodiment of the present invention, an isotopic gas analyzer as described above and wherein the exhaled breath is continuously sampled by means of a breathing tube.

There is further provided in accordance with a preferred embodiment of the present invention, an isotopic gas analyzer according to any of the previous claims and wherein the spectral ranges of the isotopes of interest are non-overlapping.

There is further provided in accordance with a preferred embodiment of the present invention, an isotopic gas analyzer comprising an array of detectors monitoring at least one of said reference, sample and zero reference channels.

There is further provided in accordance with a preferred embodiment of the present invention, an apparatus to dynamically collect selected parts of a gas sample.

There is further provided in accordance with a preferred embodiment of the present invention, an apparatus as described above and wherein the gas sample consists of multiple samples.

There is further provided in accordance with a preferred embodiment of the present invention, an apparatus as described above and wherein the gas sample is at least one breath of a subject.

There is further provided in accordance with a preferred embodiment of the present invention, an apparatus as described above and wherein the selected parts of the breath have clinical importance.

There is further provided in accordance with a preferred embodiment of the present invention, an isotopic gas analyzer consisting of an apparatus to dynamically collect selected parts of a gas sample There is further provided in accordance with a preferred embodiment of the present invention, an isotopic gas analyzer consisting of an apparatus as described above.

There is further provided in accordance with a preferred embodiment of the present invention, an isotopic gas analyzer as described above, and wherein the gas analyzer is a mass spectrometer or a non-dispersive infra-red spectrometer.

There is further provided in accordance with a preferred embodiment of the present invention, an isotopic gas analyzer as described above and wherein the non-dispersive infra-red spectrometer consists of at least one wavelength stable source of radiation which is specific to the at least one isotope.

There is further provided in accordance with a preferred embodiment of the present invention, an isotopic gas analyzer as described above, and wherein at least two samples are collected with the same isotopic ratio of the isotope of interest.

There is further provided in accordance with a preferred embodiment of the present invention, an apparatus as described above, operative as an intermediate chamber system to accumulate gas samples for analysis.

There is further provided in accordance with a preferred embodiment of the present invention, an intermediate chamber system, for accumulating at least one gas sample for analysis, consisting of a gas sensor, valving means for selecting at least one part of the at least one gas sample, and a chamber for accumulating the at least one part of the at least one gas sample.

There is further provided in accordance with a preferred embodiment of the present invention, an intermediate chamber system as described above and wherein the gas sensor is a capnographic probe, an optical probe, a pressure probe or a flow probe.

There is further provided in accordance with a preferred embodiment of the present invention, an intermediate chamber system as described above and wherein the valving means consists of at least one check valve.

There is further provided in accordance with a preferred embodiment of the present invention, an intermediate chamber system as described above and wherein the valving means consists of at least one electrically actuated solenoid valve.

There is further provided in accordance with a preferred embodiment of the present invention, an intermediate chamber system as described above and wherein the chamber for accumulating the at least one part of the at least one gas sample is rigid, flexible, or partly both rigid and flexible There is further provided in accordance with a preferred embodiment of the present invention, an intermediate chamber system as described hereinabove, and wherein at least one part of the system is disposable.

There is further provided in accordance with a preferred embodiment of the present invention, an intermediate chamber system as described above, and also consisting of dilution means for reducing the concentration of the isotopes of interest.

There is further provided in accordance with a preferred embodiment of the present invention, an intermediate chamber system as described above, and wherein the dilution means consists of a switchable gas scrubber.

There is further provided in accordance with a preferred embodiment of the present invention, an intermediate chamber system as described above, and wherein the timing of the valving means is determined by the analysis required.

There is further provided in accordance with a preferred embodiment of the present invention, an intermediate chamber system as described above, and wherein the timing of the valving means is determined by the results of the analysis.

There is further provided in accordance with a preferred embodiment of the present invention, an intermediate chamber system as described above and wherein the breath collection does not require the intervention of the subject or the operator.

There is further provided in accordance with a preferred embodiment of the present invention, an intermediate chamber system as described above and operative to collect a sample of gas for use as the reference gas in the gas analyzer.

There is further provided in accordance with a preferred embodiment of the present invention, an intermediate chamber system as described above and wherein the sample gas is collected from at least the first breath.

There is further provided in accordance with a preferred embodiment of the present invention, an intermediate chamber system as described above and wherein the at least one part of the at least one gas sample accumulated in the chamber is transferred to a gas analyzer.

There is further provided in accordance with a preferred embodiment of the present invention, an intermediate chamber system as described above and wherein the at least one part of the at least one gas sample accumulated in the chamber is transferred to a gas analyzer by means of a collection container.

There is further provided in accordance with a preferred embodiment of the present invention, a gas analyzer consisting of an intermediate chamber and wherein the breath sensor is self-calibrated by the gas analyzer.

There is further provided in accordance with a preferred embodiment of the present invention, a gas analyzer consisting of an intermediate chamber, and which can be self-calibrated by generating by means of the intermediate chamber a group of diluted samples with the same isotopic ratio, from a single sample of a subject, and comparing the isotopic ratios measured by the gas analyzer with the fixed isotopic ratio of the samples, and using the results of this comparison to recalibrate the gas analyzer There is further provided in accordance with a preferred embodiment of the present invention, a gas analyzer as described above, and wherein the samples are breath samples.

There is further provided in accordance with a preferred embodiment of the present invention, a gas analyzer which is self-calibrated by correlating the spread in the measured isotopic ratio of samples from negative patients, with the spread in the concentration of at least one of the isotopes in the same samples.

There is further provided in accordance with a preferred embodiment of the present invention, an intermediate chamber system for collecting a multiplicity of breaths.

There is further provided in accordance with a preferred embodiment of the present invention, a as analyzer consisting of an intermediate chamber operative to accumulate samples of gas to be analyzed, and wherein the end concentration of the accumulated samples is determined by the analyzer.

There is further provided in accordance with a preferred embodiment of the present invention, an intermediate chamber system as described above and capable of achieving a predetermined concentration and volume even with temporally changing breaths.

There is further provided in accordance with a preferred embodiment of the present invention, an intermediate chamber system as described above and capable of collecting breaths from the plateau region of the carbon dioxide wavefront of a subject.

There is further provided in accordance with a preferred embodiment of the present invention, an intermediate chamber system consisting of a computer controlled gas handling system consisting of a gas sensor, a first solenoid valve, a second solenoid valve, a gas scrubber, a pump, at least one collection container, and at least a third solenoid valve, the first solenoid valve directing gas into one of two paths, one of which discards the gas, and the other of which passes it either through the gas scrubber to the second solenoid valve, or directly to the second solenoid valve, the pump pumping gas from the second solenoid valve into the at least one collection container, the third solenoid valve being operative to pass gas in the at least one collection container for analysis.

There is further provided in accordance with a preferred embodiment of the present invention, a method for accumulating at least one sample of gas to be analyzed, wherein the end concentration of the accumulated samples is determined by the analyzer, and consisting of the steps of measuring the gas concentration, deciding whether to accumulate the at least one sample, calculating the content of the accumulated gas, and deciding whether to continue collecting further samples according to whether the accumulated gas has reached a desired concentration and volume.

There is further provided in accordance with a preferred embodiment of the present invention, a method for accumulating at least one sample of gas to be analyzed, wherein the end concentration of the accumulated samples is determined by the analyzer, as described above, and wherein and said at least one sample of gas to be analyzed is at least one breath sample.

BRIEF DESCRIPTION OF THE DRAWINGS

The present invention will be understood and appreciated more fully from the following detailed description, taken in conjunction with the drawings, in which:

FIG. 1A is a schematic view of an NDIR spectrometer according to a preferred embodiment of the present invention, showing the two separate isotope channels, each with their own lamp, absorption chambers, and fiber optical zero calibration channels, and with one common detector for all measurement channels.

FIG. 2 is an isometric view of the NDIR spectrometer shown in FIG. 1A, showing the two separate frequency modulated isotope light sources, the four measurement channels, and a single detector.

FIG. 9 shows the timing diagram and signal outputs for an alternative synchronous detection scheme, wherein both lamps are modulated at the same frequency by means of one or two RF exciters, and phase discrimination is used to differentiate between two separate isotope channels.

FIGS. 10A to 10E show the timing diagrams which explain how the separate 12C and 13C signals are extracted electronically using the single lamp exciter scheme shown in FIG. 9.

FIG. 32 shows a mechanical check valve assembly incorporating a reservoir with constant volume, for providing a constant sampling flow rate.

FIG. 33 shows a mechanical check valve assembly similar to that shown in FIG. 32, except that it incorporates a reservoir with a variable volume for providing a system for use with a variable sampling flow rate.

FIG. 34 shows a double reservoir intermediate chamber breath sampling device.

DETAILED DESCRIPTION OF PREFERRED EMBODIMENTS

Figure 1B:
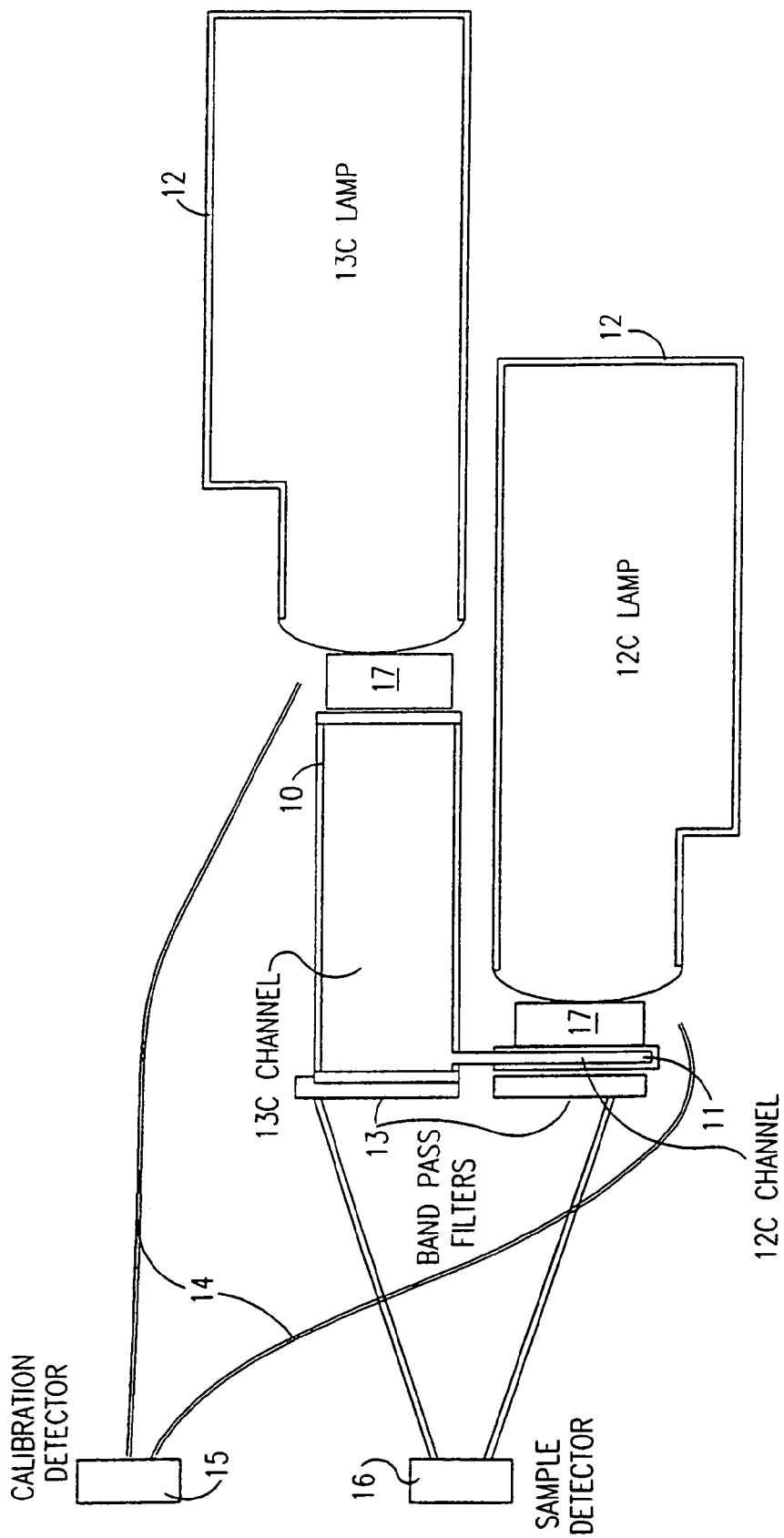
FIG. 1B shows the same NDIR spectrometer but including a beam homogenizer.

Reference is now made to FIG. 1A which shows a schematic view of the NDIR spectrometer of the breath analyzer, constructed and operative according to a preferred embodiment of the present invention. (It should be noted that in all of the drawings, the symbols $12CO_2$ and $13CO_2$ have been abbreviated by the symbols 12C and 13C respectively.) This embodiment uses two lamps and one detector for the signal and reference channels, and a further detector for stabilizing the lamp outputs, as will be described below. The $13CO_2$ chambers 10, both sample and reference, are considerably longer than the $12CO_2$ chambers 11 in order to provide sufficient absorption signal from the small quantity of $13CO_2$ present in the sample gas.

The IR lamps 12 are gas discharge lamps as described in U.S. Pat. No. 5,300,859. Each of them is filled with an essentially pure filling of the isotopic gas, either $13CO_2$ or $12CO_2$. As a result, each lamp emits a radiation spectrum substantially of the appropriate isotope only. The lamps are each modulated at a different frequency, by means of modulating the RF exciter power supply to each lamp. By this means, the separate frequency components of the combined signal appearing on the single signal detector can be separated by means of synchronous detection techniques, as will be explained below.

However, the highest level of $13CO_2$ enrichment available is about 99.3%, which means that the $13CO_2$ lamp spectrum still contains a small percentage of $12CO_2$ spectral lines. In fact, the situation is more serious than the percentage enrichment implies, since the remaining 0.7% of $12CO_2$ produces several times that level of $12CO_2$ spectral lines, because of interaction effects in the gas discharge. Since the sample breath analysis has to detect very small changes in the $13CO_2/12CO_2$ ratio, and since the percentage of $13CO_2$ is so much smaller than that of $12CO_2$, even a small residue of $12CO_2$ lines in the incident light will seriously affect the accuracy of the measurement. For this reason, an absorbing filter filled with $12CO_2$ gas is placed in the $13CO_2$ channel, so as to effectively absorb all of the remaining $12CO_2$ lines in the $13CO_2$ source. As an alternative, an optical bandpass filter 13 can be used for filtering out the interfering spectral lines as explained above. Another possible reason for the use of filters is to remove part of the emission. Part of the emission is removed in such a way that light passing through the 13C channel cannot be absorbed by the 12C and vice versa. This addresses the problem of cross sensitivity. Another approach to address this problem is to lower the pressure to avoid absorption of the 13C light by the broad absorption line of 12C at atmospheric pressure.

To follow short term fluctuations in lamp intensity, it may be necessary to monitor the light output from each lamp constantly and the level used for correcting the measured absorption in the sample channels. The luminous output from each lamp is therefore sampled by means of optical fibers 14. These signals are measured on the calibration detector 15, and the output used as a reference signal for normalizing the sample signals to a constant level. Although both fibers go to one detector, since the optical signal on each fiber is modulated at a different frequency, depending on the modulation frequencies of the two lamps, the two signals can be separated by means of standard synchronous detection techniques. This procedure overcomes the problem of lamp intensity drift in this embodiment, which uses two separate lamps for each isotope.

In cases where improved light uniformity is advantageous, a beam homogenizer 17, such as a fiber, a fiber bundle, or a kaleidoscope can be placed in the optical path, as shown in FIG. 1B.

The sample detector 16 is preferably a PbSe infra-red detector, which is cooled by means of a one or two stage thermoelectric cooler to between −10° C. to −50° C. This is done to improve the sensitivity, stability and noise performance of the detector at the $CO_2$ wavelengths in the region of 4.2 to 4.45 μm. In spite of cooling the detectors to a fixed and low temperature, they still exhibit some drift with time, both electrically and thermally. However, since the measurement is done on ratios of channels, the effects of this drift tend to be complementary, and it is not a major source of inaccuracy in this embodiment of the breath test system.

FIG. 2 shows an isometric view of the NDIR spectrometer. The compact construction of this embodiment is clear from this drawing. The analysis chambers are built into a block of aluminum 21. The $13CO_2$ chambers 22, both sample and reference, are considerably longer than the $12CO_2$ chambers 23 as explained above. The four absorption chambers sample and reference for each of the two isotopes are visible in the end plate 24 of the analyzer block. A thin steel shutter 25 slides along a thin recess in the end plate for switching the measurement between the reference channel and the sample gas channel. This is done approximately every 10 to 60 sec., depending on the measurement situation encountered. This time is taken as a compromise between the need to perform averaging over a sufficiently long time to obtain a stable and representative signal, and the need to perform the reference and sample measurements sufficiently close in time that the system conditions do not change appreciably between measurements. The axes of the isotope lamps 26 and the absorption chambers 22, 23 are aligned such that the output light beams from the four channels are all directed into the single detector 28 by means of the light cone 27.

Figure 3:
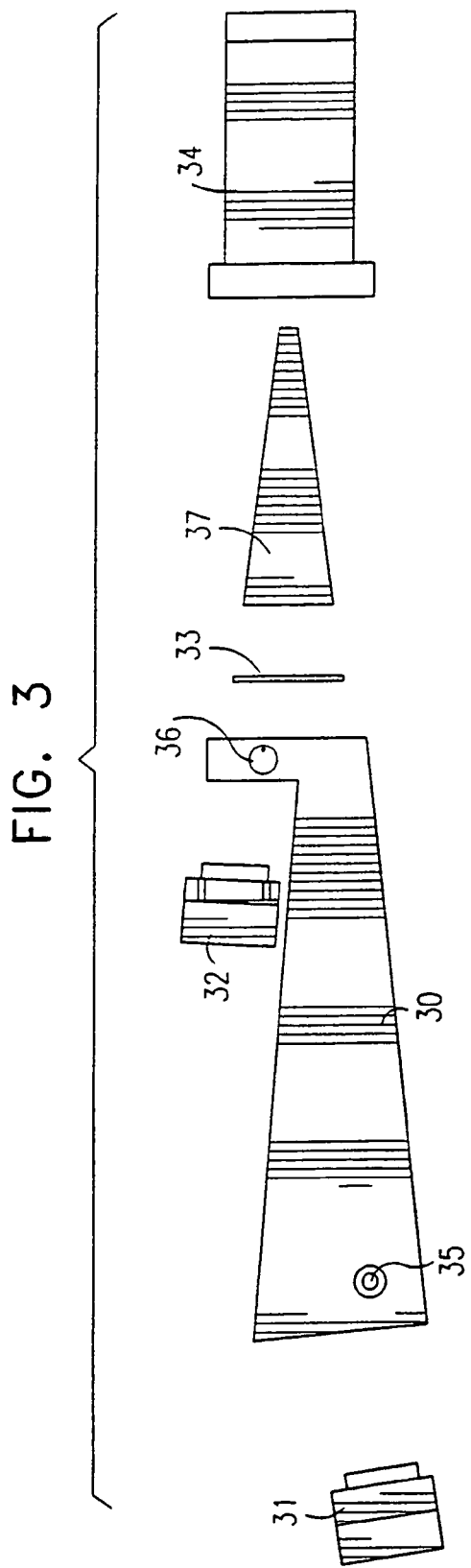
FIG. 3 is an exploded plan view of the NDIR spectrometer shown in FIG. 2, showing how the constituent parts fit compactly together.

FIG. 3 shows an exploded cut-away view of the spectrometer shown in FIG. 1 and FIG. 2. The chamber block 30, isotope lamps 31 32, shutter 33, light cone 37 and the detector cover 34 are shown. The gas inlet 35 and outlet 36 to the sample chamber are positioned in the side of the block, and the gases led to their respective chambers by means of internal passages drilled into the aluminum block.

Figure 4:
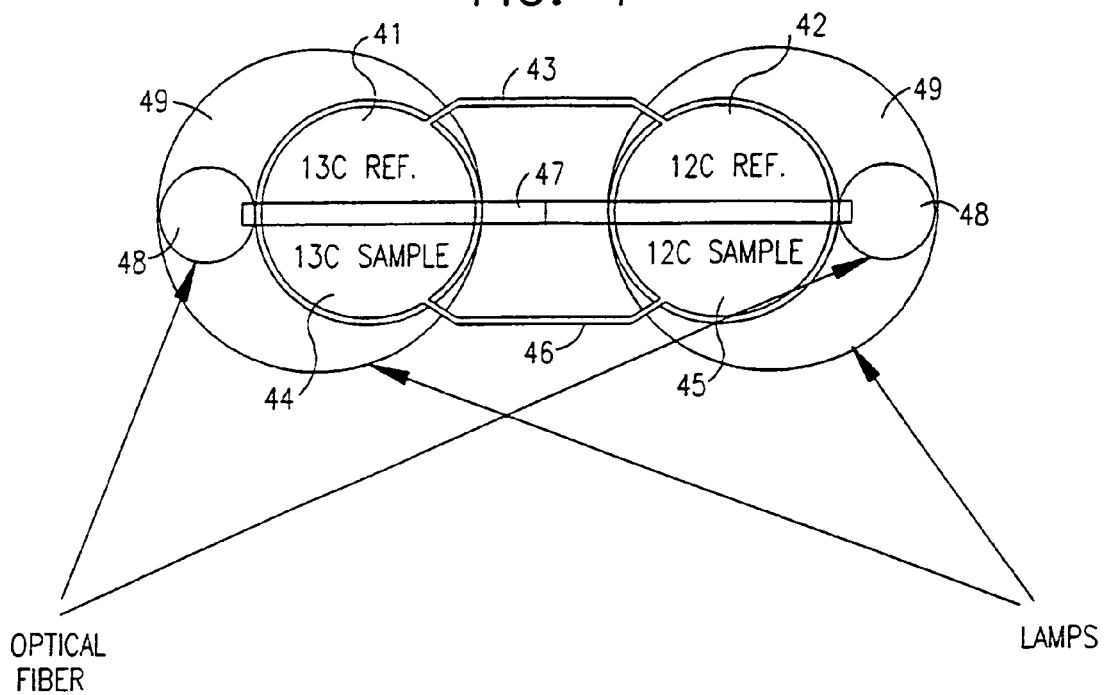
FIG. 4 is a cross sectional view of the NDIR spectrometer, showing the six measurement channels—the reference, sample and zero-calibration channels for each of the two isotopes.

FIG. 4 shows a cut-away cross section of the absorption chambers of the NDIR spectrometer shown in FIGS. 1 to 3. The two reference absorption chambers 41 42, are connected together pneumatically by means of a tube 43, so that the two reference channels contain the same gas at the same pressure. The sample absorption chambers 44 45 are similarly connected by means of tube 46. In addition, both the $13CO_2$ and the $12CO_2$ channels of the NDIR spectrometer are thermally strapped together by means of a thick shunt of conductive metal 47, such that the gases in both isotopic channels are thermally as close as possible to being in equilibrium. This feature assists in attaining good thermal stability to the measuring system. The reference and sample chambers can be filled with a flowing gas or a static filling, or any combination thereof. The reference gas can be a gas mixture with a known isotopic ratio, or if more convenient, a sample of the first breath in the case of a breath analyzer. The optical fibers 48 which monitor the lamp 49 intensities are located such that they do not interfere with the entry of the lamp light to the analysis chambers.

Figure 5:
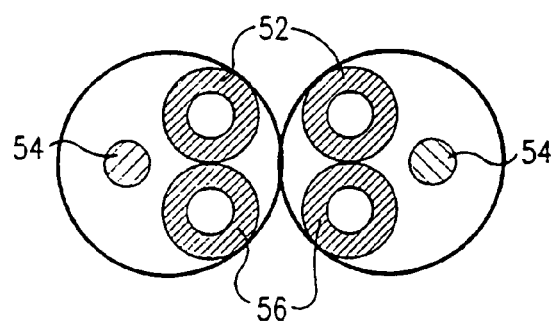
FIG. 5 shows a preferred constructional method for the NDIR spectrometer, using extruded stainless steel pairs of tubes for the gas channels, embedded in a cast aluminum structure.

FIG. 5 shows the materials and method of construction of NDIR spectrometer absorption chambers according to a preferred embodiment of the present invention. The materials have been selected to provide compactness with high strength and low cost construction. The absorption chambers are constructed of an extruded section of a pair of stainless steel tubes 52. Electro-formed light pipes could also be used instead of stainless steel tubes. The whole assembly, with the fiber optical monitor fibers 54, is mounted inside a light aluminum profile structure 56, which provides mechanical stability together with low cost and low weight.

Figure 6:
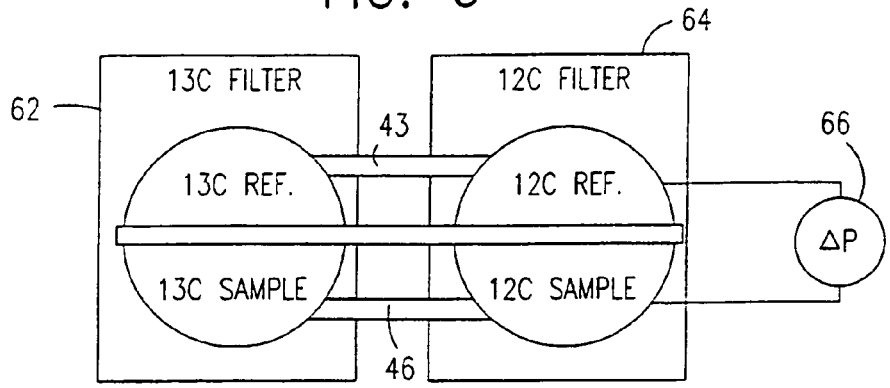
FIG. 6 is a functional cross sectional view of the NDIR spectrometer, showing how the two reference channels and the two sample channels are respectively pneumatically connected to each other by means of gas pipes, and the differential pressure measurement between them, and how the $13CO_2$ and $12CO_2$ chambers are connected thermally.

FIG. 6 is a view taken from the front of the gas channels, showing the $13CO_2$ filter 62 located in front of the $13CO_2$ gas channels, and the $12CO_2$ filter 64 located in front of the $12CO_2$ channels. These filters function to remove unnecessary emission regions from the lamp, and to prevent thermal background emission from reaching the detector. A high sensitivity differential pressure sensor 66 is connected between reference and sample channels. It is used to ensure that the pressure in the reference and sample channels, both being at a pressure lower than atmospheric, are equated, if advantageous for the measurement. In addition, the reference channel also includes an absolute pressure sensor, for monitoring the attainment of the reduced pressure required to achieve good measurement sensitivity.

Figure 7:
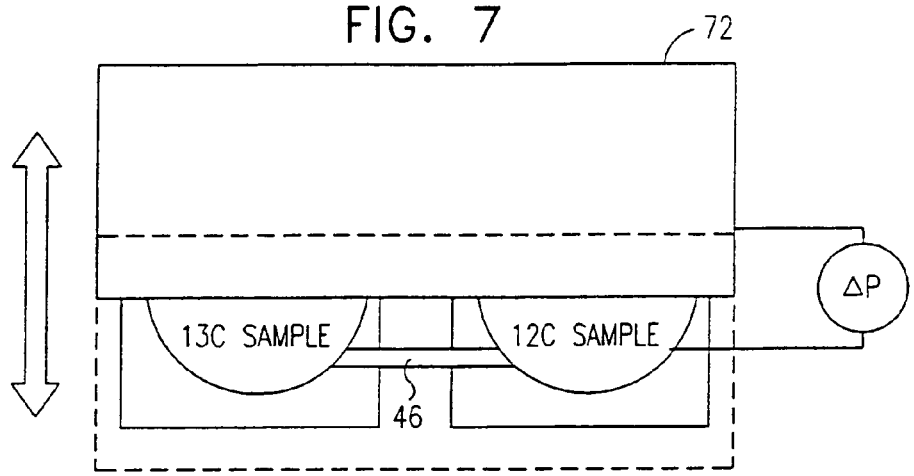
FIG. 7 is a schematic illustration of the shutter used to alternately measure the sample and reference channels.

FIG. 7 illustrates how the shutter 72 is used to select the measurement channel in use. At the beginning of each sample measurement, the shutter is in the lower position, thereby allowing the lamps to illuminate the reference channels, and to obtain a baseline reference measurement. This measurement is a monitor to environmental changes taking place in the system, changes in the lamp light spectrum, changes in filter characteristics, or in detectors or electronics characteristics, all of which should be fairly constant. If the reference measurement does show change, a correction factor is used to compensate the sample channel readings for the change in environmental conditions. After completion of the reference measurement, the shutter is moved up into the position shown in the drawing, and the sample measurement taken from the sample channels. Once this sample measurement has been obtained with sufficient accuracy, the sample is removed pneumatically, and the analyzer is ready for receiving its next measurement sample. The chamber purging and the conditioning of the next sample are executed during the reference measurement. This is performed approximately once per minute.

Figure 8:
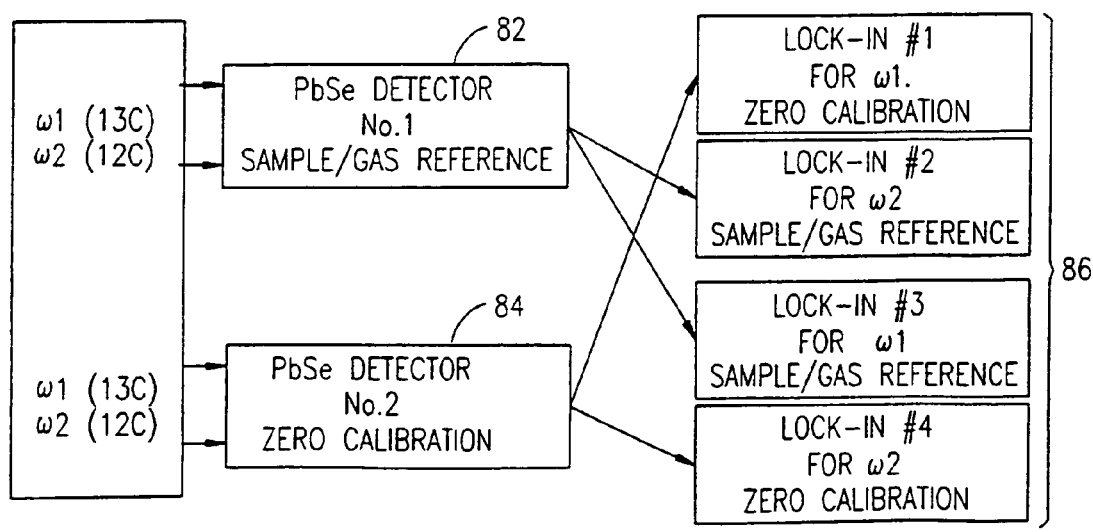
FIG. 8 is a schematic view of the synchronous detection scheme used in the spectrophotometer described in FIG. 1, wherein each of the lamp sources is modulated at a different frequency, and four lock-in amplifiers are used for the four separate channels.

FIG. 8 is a schematic view of the electronic method whereby can be discriminated. The $13CO_2$ lamp is modulated at frequency $\omega 1$, while the $12CO_2$ lamp is modulated at frequency $\omega 2$. sample/gas and zero calibration has its own detector 82 84 respectively. Four synchronous detection channels 86, using devices such as lock-in amplifiers, digital signal processors, software packages, or analog or digital filters, are required to extract the four modulated signals sample/gas reference and zero calibration of the two isotopic lamps. The trigger signals for each of these lock-in amplifiers, are taken from the driver signals of the lamp source modulation power supply. Modulation frequencies are in the range of 1 to 200 Hz, with 70 Hz. being a typical value.

It is also possible to modulate both lamps at the same frequency, either using one RF exciter switched between the two lamps, or using two exciters switched on and off in antiphase, and to use phase information in order to discriminate between the two signals from each lamp. This is illustrated in FIG. 9, which shows a continuous train of modulating pulses 92 applied alternately to each lamp, and the resulting train of alternating signals 94 on the detector. An instrument such as a box-car integrator is used to extract the signal from each isotopic lamp separately. This detection scheme has an advantage in that there is less sensitivity to drift in exciter output, and that there is no electronic cross sensitivity between the two isotopic lamps, since each is separated in time, and not in frequency.

The method whereby the two different isotopic channels are separated electronically, when using the single exciter modulation scheme shown in FIG. 9, is illustrated in FIGS. 10A to 10E. FIG. 10A represents the continuous stream of square wave pulses, which are alternately directed to the $13CO_2$ lamp or the $12CO_2$ lamp, as shown in FIGS. 10B and 10C respectively. These pulse trains are convoluted with the output signals from the detector, and the resulting outputs are respectively a train of $13CO_2$ pulses as shown in FIG. 10D, or a train of $12CO_2$ pulses as shown in FIG. 10E. The convolution is performed by a box-car integrator, or a phase sensitive detector.

Figure 11:
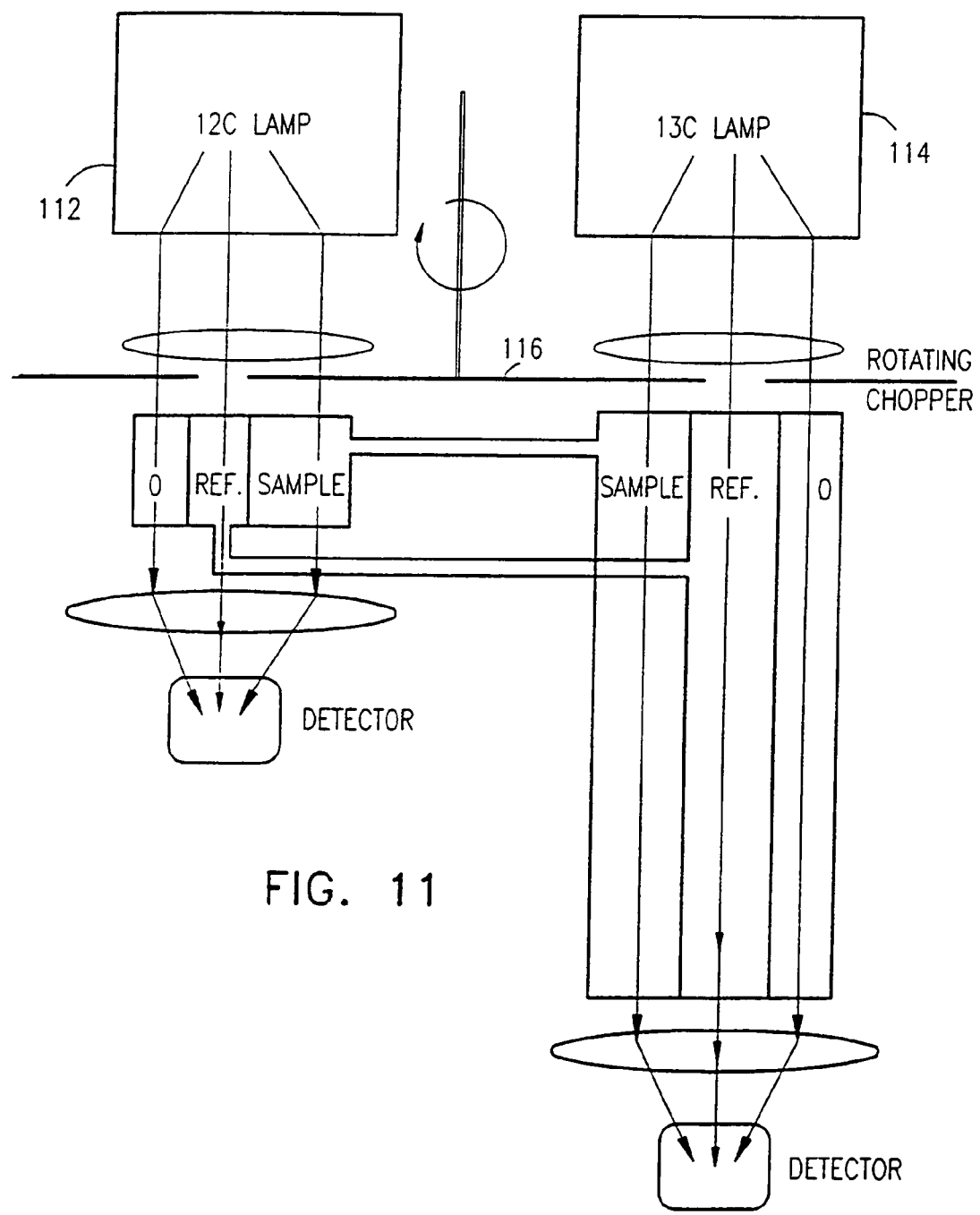
FIG. 11 is a schematic view of an alternative NDIR spectrometer design, using two lamps as before, but with two separate detectors, one for each channel. The signal modulation is performed in this case using a rotary chopper to modulate the light.
Figure 12:
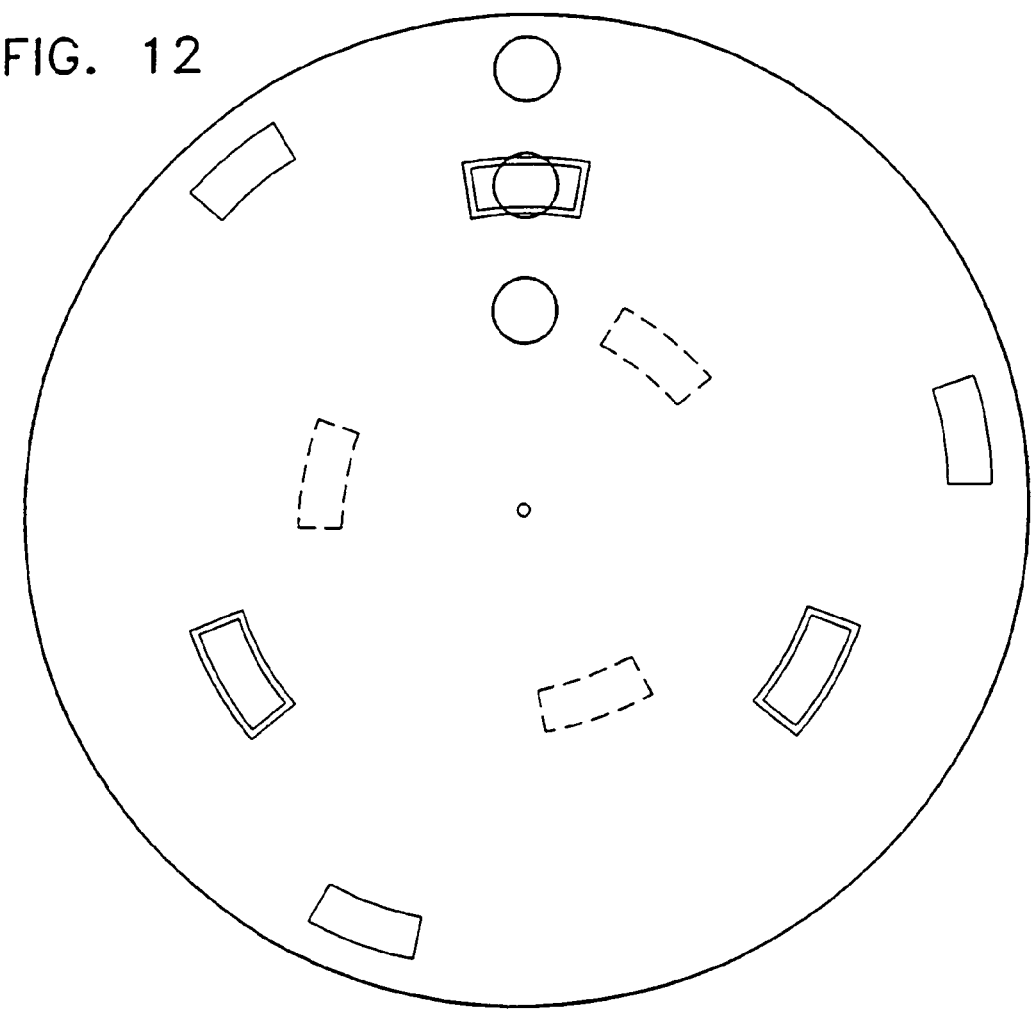
FIG. 12 shows a chopper design suitable for use in the NDIR spectrometer shown in FIG. 11.
Figure 13:
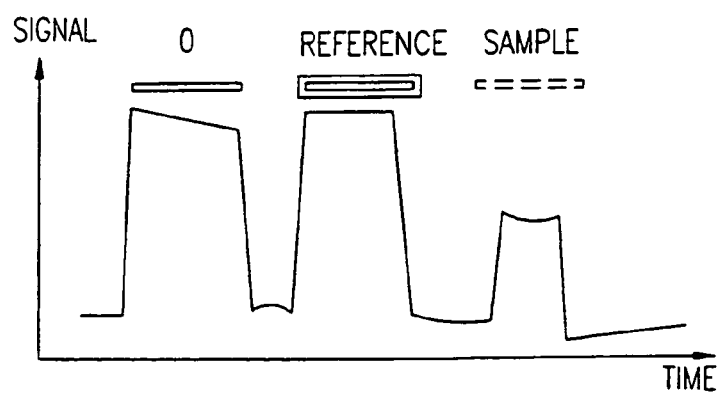
FIG. 13 is a representation of the three signals obtained from the reference, sample and zero calibration channels, using the chopper shown in FIG. 12.

A further preferred embodiment of the present invention is shown in FIG. 11. As previously, two lamps are used, one for each isotope 112 114. Each isotope has its own complete measuring system, with sample, reference and calibration channels, connected only by means of the mechanical, thermal and pneumatic connections as previously described. In order to reduce the effects of detector drift, one detector is used for all three signals in each isotope measurement channel. In order that each detector can differentiate between the three types of signal received from its light source, a mechanical chopper 116 is used. The chopper can differentiate between the three channels either by means of frequency discrimination, or by means of phase discrimination. In the former case, the chopper has three sets of holes, each set at a different radial distance from the center, and each set having a different number of holes. In this way, three different frequencies for different spatial regions of the source lamp are defined, where these three regions correspond to the three different channels. If phase discrimination is used, the chopper has three rows of slots, each at different radial distance corresponding to the location of the three channels, and with the sets of slots arranged at fixed angular intervals around the chopper. A chopper for use in phase discrimination is shown in FIG. 12. In FIG. 13, the signal received at the detector of either isotope channel when using such a chopper, is shown as a function of time.

There are a number of disadvantages of frequency discrimination choppers when compared to phase discrimination choppers. The first problem is that it is very difficult to provide phase sensitive signal processing with a sufficiently high selectivity for the discrimination required by the present system. If the selectivity of the phase sensitive signal processing is insufficient, enough of the signal of the unwanted frequency will be detected to render the measurement inaccurate. In order to provide good detection accuracy for the $13CO_2$ in the sample breath, a selectivity of 1:20,000 is required, which is difficult to achieve.

Furthermore, an electronic cross sensitivity effect is present in the detectors, which may have a non-linear response at the upper and lower extremities of their range. Therefore, if a strong signal is present at one frequency, it may shift the operating point of the detector in such a way that it behaves non-linearly to a weak signal of a different frequency imposed upon it. This would severely affect the measurement accuracy.

On the other hand, there is also a disadvantage to phase discrimination choppers. Only one channel can be open at any one time, unlike frequency discrimination choppers, wherein all the channels can be transmissive at any time, all being at different frequencies. Consequently, the phase discrimination method has a lower duty ratio, and therefore a less sensitive detection capability.

Both of the above embodiments according to the present invention, use two lamps, and calibration detectors are used to eliminate the effects of source lamp variation, as described above.

Figure 14:
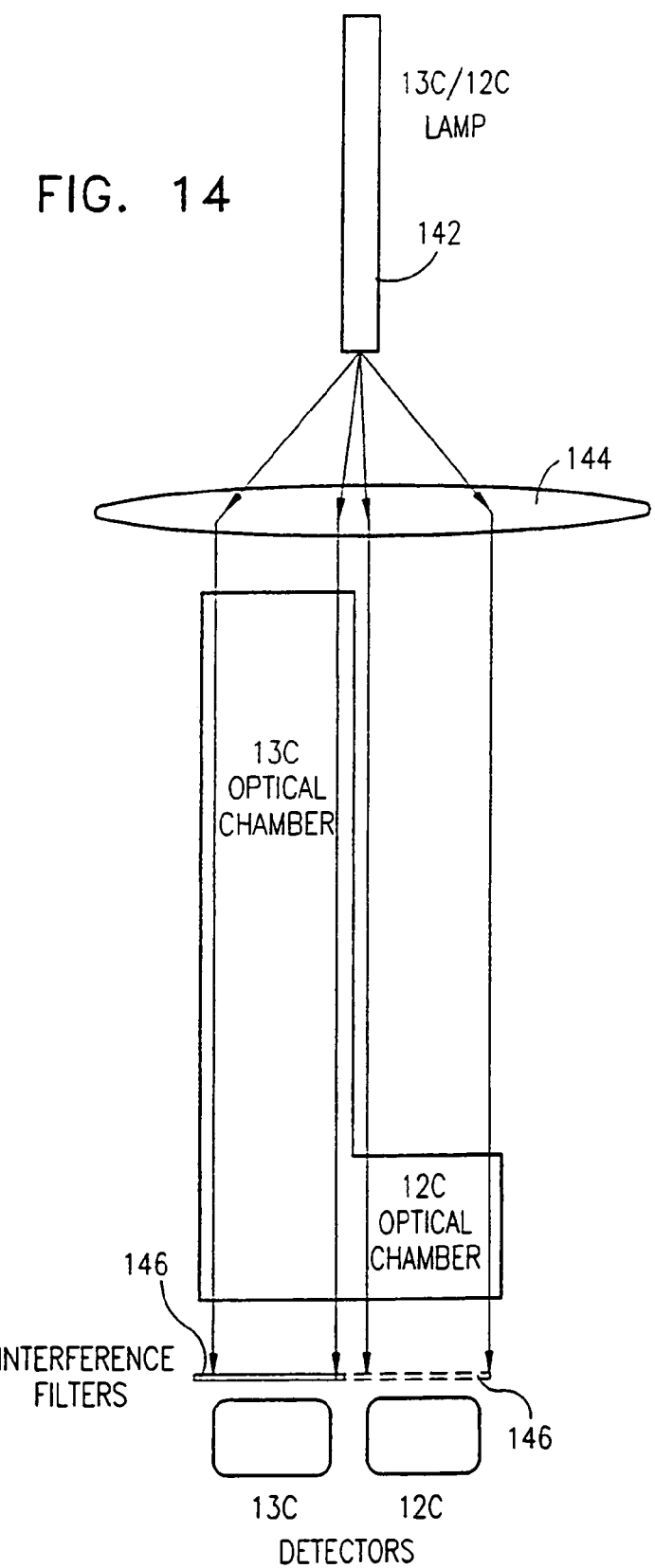
FIG. 14 shows an alternative NDIR spectrometer design wherein only one lamp is used, this lamp being charged with a mixture of 12C and 13C such that it emits the spectra of both isotopes. Two detectors are used in this embodiment. Interference filters are used to discriminate between the two isotope channels.
Figure 15:
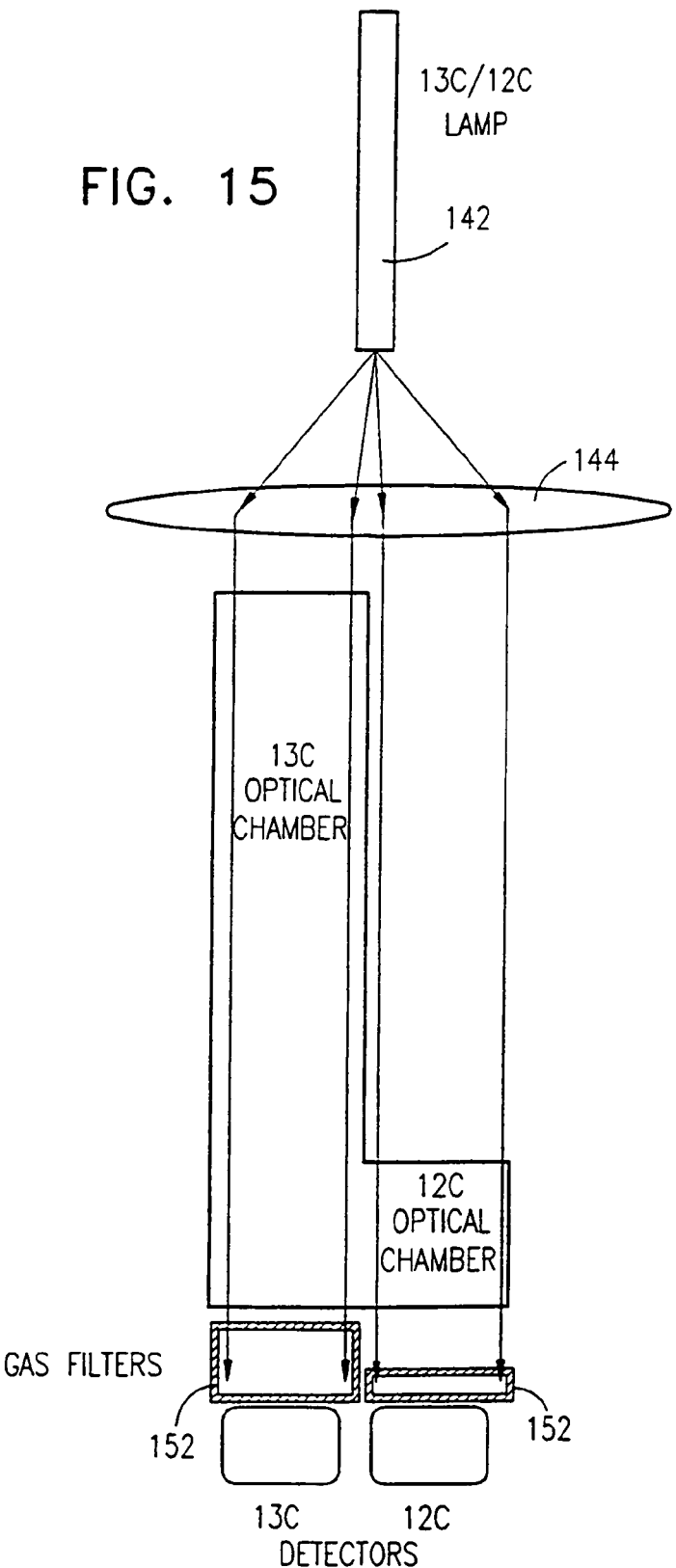
FIG. 15 shows an NDIR spectrometer similar in design to that in FIG. 14, but using gas filters instead of interference filters.

FIGS. 14 and 15 show preferred embodiments of an NDIR spectrometer constructed and operative according to a preferred embodiment of the present invention, wherein only one lamp source is used. The lamp 142 is filled with a mixture of the two isotopes whose ratio is to be measured, in this embodiment $13CO_2$ and $12CO_2$. Since only one lamp is being used, changes in operating conditions or environmental effects, take place in both channels simultaneously, and therefore have greatly reduced effects on the measurement accuracy. In both of the FIGS. 14 and 15, the light from the lamp source of the NDIR spectrometer is collected and collimated into two separate beams by means of an entry lens 144. Each beam then passes through its relevant absorption chambers, and via the wavelength filters 146 to the detectors. These may be separate detectors, or preferably, parts of one larger pixelated detector, in which case detector drift will be reduced. In the embodiment of FIG. 14, optical interference filters are used for filtering out the unwanted spectral lines from the light in each isotope channel, while in FIG. 15, gas filters 152 are used. A combination of gas and optical filters can be used. Signal modulation is performed using a mechanical chopper operating either in the frequency or the phase chopping mode, or by means of modulating the lamp and synchronously detecting the signal on each detector separately, while switching between the reference and sample channels by means of a shutter.

Figure 16:
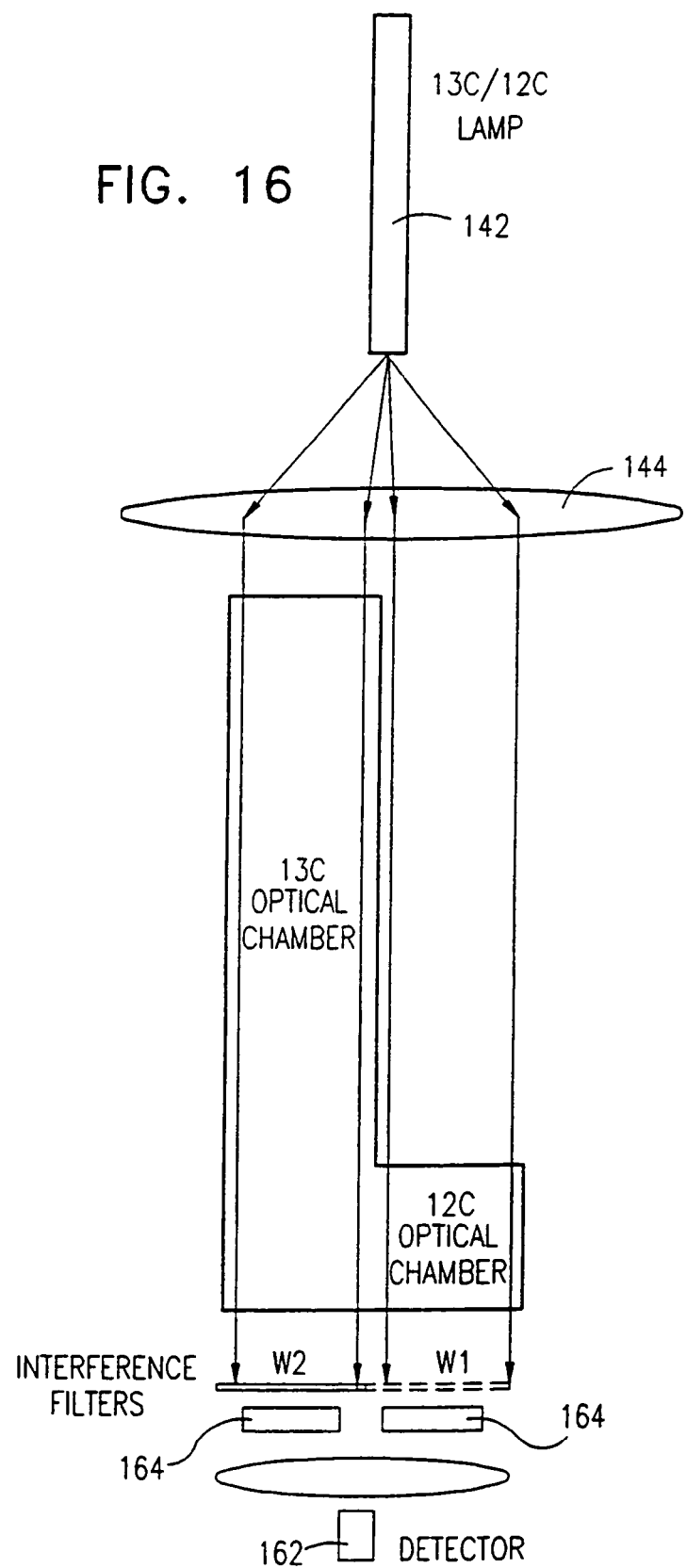
FIG. 16 illustrates a further NDIR spectrometer design using only one lamp and one detector, wherein the light is switched alternately from each of the four channels to the detector by means of spatial light modulators.

A further embodiment of the present invention is shown in FIG. 16. In this embodiment, a further reduction in the sensitivity of the system to external and environmental conditions is achieved by the use of only one detector 162 for both isotope channels, instead of the two used in all of the previous embodiments. The one lamp—one detector embodiment represents the system with the best environmental stability with respect to component drift.

In general light valves may be used in gas absorption measurements wherein a light source cannot be modulated internally or cannot be modulated fast enough, or wherein more than one channel is viewed by one detector, or wherein the number of channels monitored is larger than the number of detectors. In particular, in this application, discrimination between the signals from the five separate channels—two reference, two sample and one lamp level calibration signal—is achieved by means of an SLM, a spatial light modulator 164. Such a spatial light modulator can preferably be a liquid crystal matrix placed between polarizers, or a DMD (Digital Mirror Device) pixelated mirror, such as those produced by Texas Instruments Inc. of Houston, Tex., or a deflecting membrane device, such as produced by Optron Inc, or an active reflecting device such as those produced by Lucent Technologies Incorporated. The function of the spatial light modulator is to modulate the light from each channel at a different phase or frequency, according to a predetermined sequence and frequency. This sequence and frequency is conveyed to the phase sensitive detector used to discriminate between the various signals, in order to extract the signal information relevant to each measurement channel. The SLM can be operated at high frequency, thereby reducing the noise contribution to the signal. The use of an SLM, effectively avoids the problem mentioned previously of the limited selectivity of phase sensitive signal processing, since very widely differing frequencies of modulation with negligible electric cross sensitivity can be used.

Figure 17:
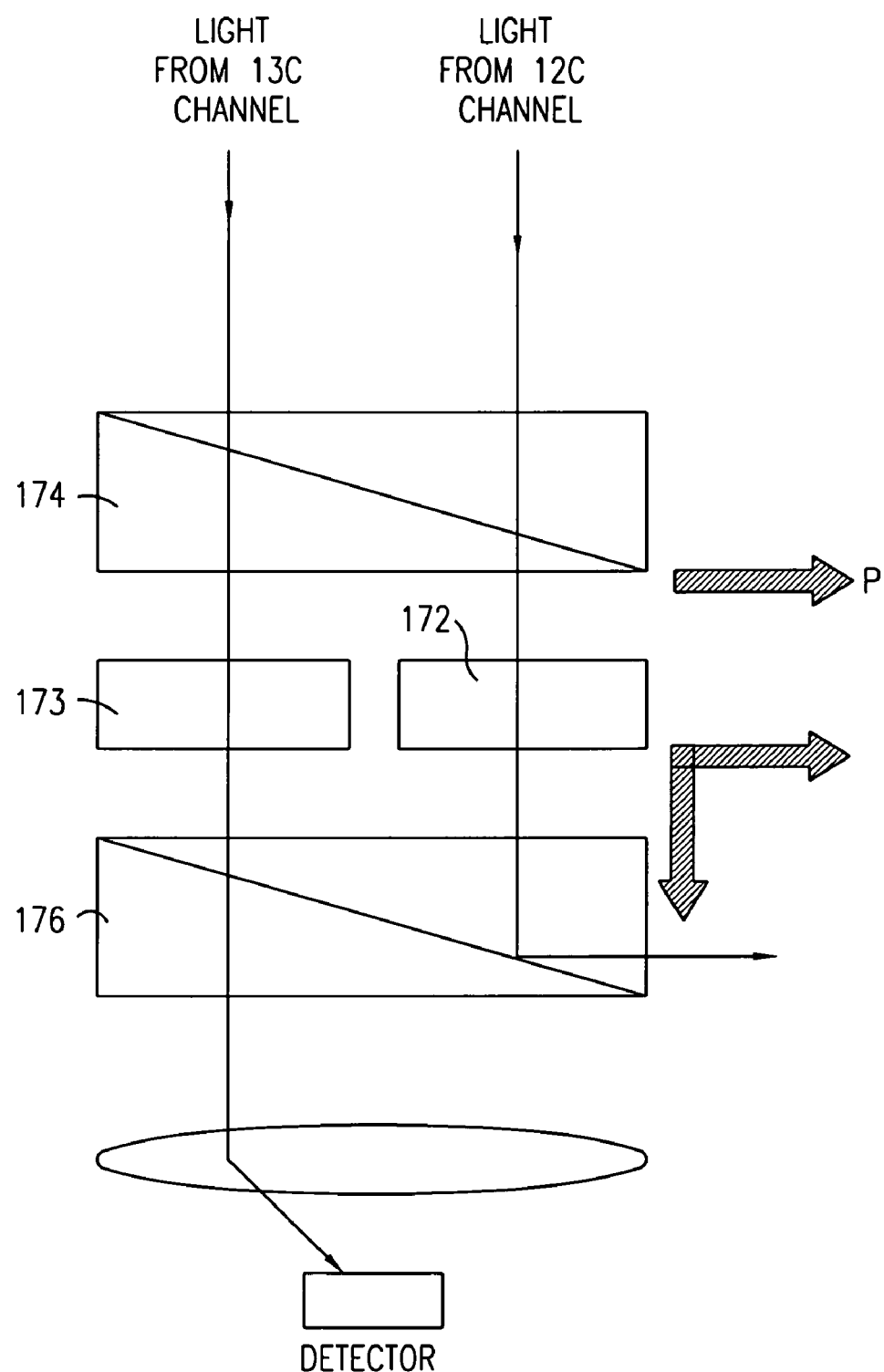
FIG. 17 shows a possible arrangement of spatial light modulators for use in the embodiment shown in FIG. 16. The active elements shown are liquid crystals disposed between pairs of polarizers.

FIG. 17 illustrates a preferred embodiment of such an SLM, using transmission liquid crystal elements 172, 173. The light from the reference and sample chambers for each isotope channel is passed through a polarizer 174, where it attains a linear direction of polarization. If a particular liquid crystal element 172 is activated, the light passing through that element will attain a polarization switched by a further 90°, so that on passage through another polarizing element 176, the light is cut off. In this way, each liquid crystal element acts as a fast electrically operated switch.

Figure 18:
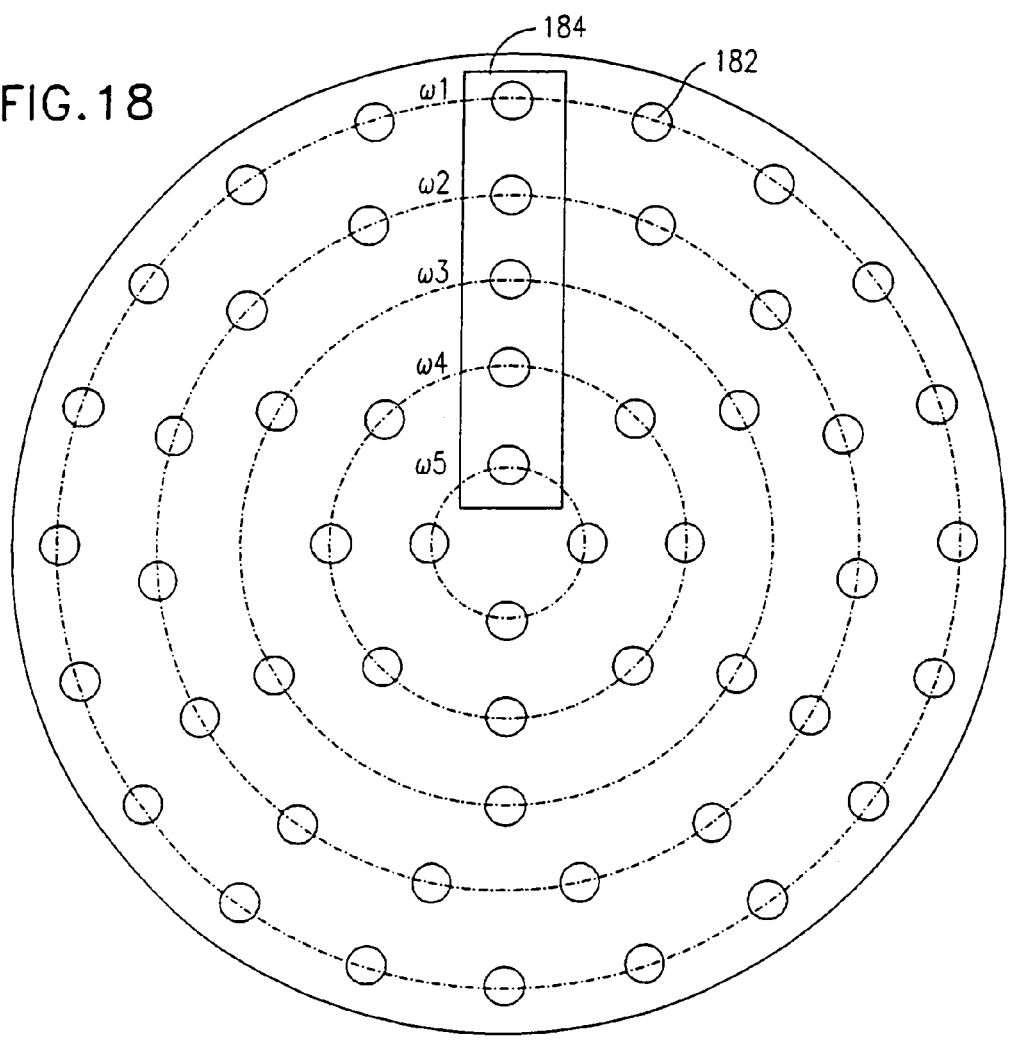
FIG. 18 shows a mechanical spatial chopper which can be used in the NDIR spectrometer embodiment shown in FIG. 16, as an alternative to electronic spatial light modulators. The chopper design shown is able to chop the light emerging from each of the five signal channels, two sample channels, two reference channels, and a zero calibration channel, at a different frequency, and thereby to discriminate between them in the single detector.

It is also possible to use a mechanical chopper instead of an SLM for spatially switching the various signal channels into the detector. FIG. 18 is a schematic example of such a chopper. Each row of holes 182 is located at a radius from the center such that each row falls exactly on the location 184 of one of the five optical signal channels, labeled φ1 to φ5. In FIG. 18, the optical signal channels are shown schematically in one straight line for simplicity, whereas in a real embodiment, they will be staggered to fall in their correct geometrical location in the NDIR spectrometer. The frequencies are chosen such that there are no low order common harmonics between them, and the further apart the frequencies, the better the discrimination. In this case, the system may be constructed to generate a phase difference as in FIG. 12.

Figure 19:
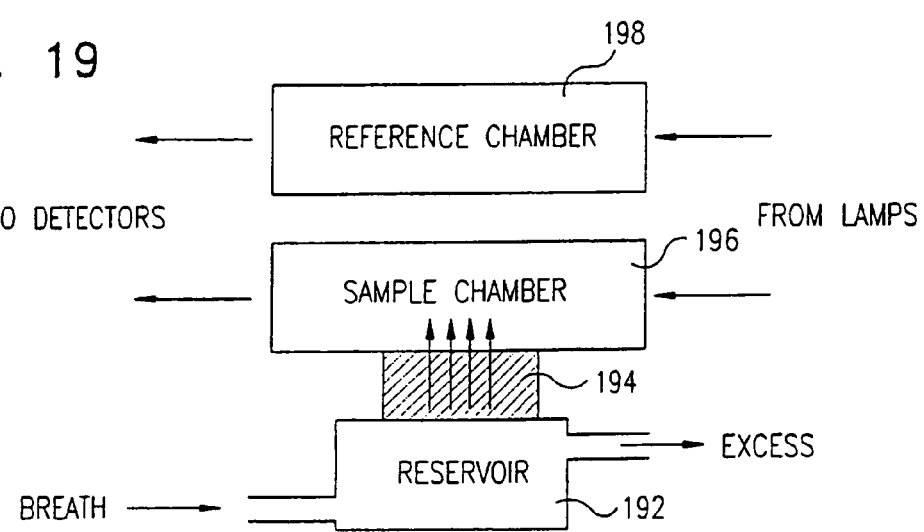
FIG. 19 is a representation of an osmotic system for ensuring that the partial pressure of the $CO_2$ in the sample chamber and the reference chamber are equal.
Figure 20A:
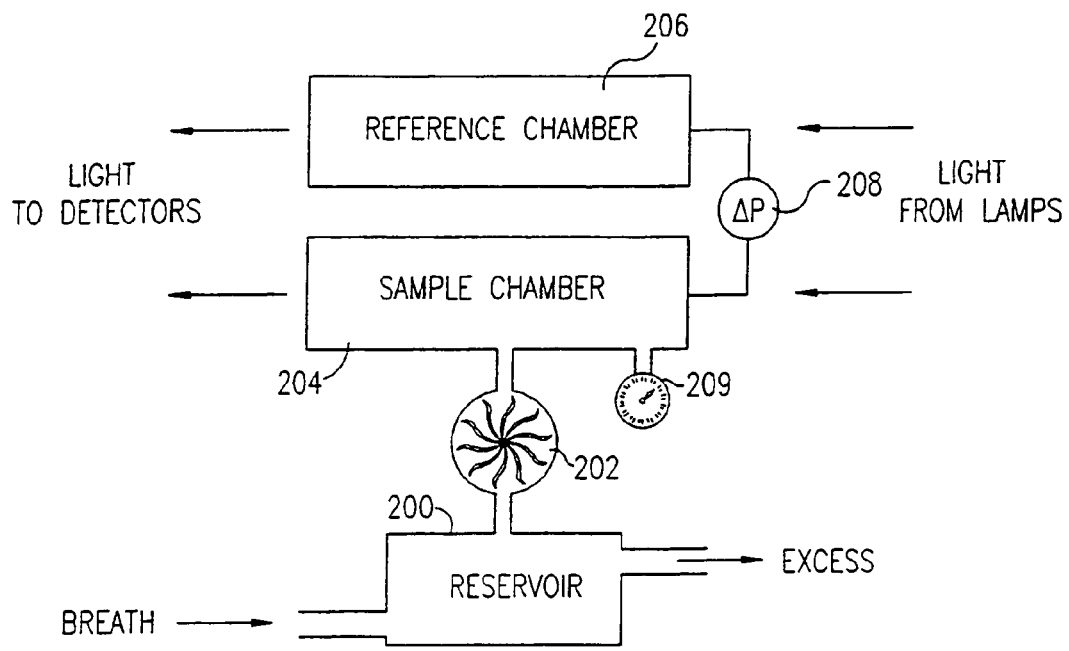
FIG. 20A is a representation of a pumped system for ensuring that the partial pressure of the $CO_2$ in the sample chamber and the reference chamber are close.

FIGS. 19 and 20A show two alternative preferred embodiments for ensuring that the partial pressure of the $CO_2$ in the sample chamber and the reference chamber are close, in order to ensure that the $13CO_2$ absorption is measured accurately and under close conditions in both chambers. The embodiments described are of a breath test analyzer application, this being one of the common uses of isotopic gaseous analysis of $CO_2$, but the construction and methods shown are applicable to any isotopic gas analysis.

In the embodiment shown in FIG. 19, the sample breaths are exhaled into a reservoir 192, which is connected to the sample absorption measurement chamber by means of a membrane 194 permeable to $CO_2$. The sample chamber 196 is initially filled with an inert background gas such as pure nitrogen at atmospheric pressure. The reference chamber 198 is filled either with the first breath sample, or with a predetermined reference gas mixture. The $CO_2$ from the reservoir diffuses into the sample chamber until the $12CO_2$ partial pressure as determined by the $12CO_2$ absorption measurement itself, is equal in the sample and reference chambers. When this point is reached, the membrane passage is sealed off by valving means, and the $13CO_2$ measurement is performed accurately in the knowledge that the same conditions exist in the sample and reference chambers.

FIG. 20A illustrates another preferred embodiment in which the partial pressure of the $12CO_2$ in the sample chamber and the reference chamber are equalized. As in the embodiment shown in FIG. 19, the sample breaths are exhaled into a reservoir 200. This reservoir is connected by means of a pump 202 to the sample chamber 204, which, unlike the embodiment of FIG. 19, is initially evacuated. The pump is operated until the $12CO_2$ partial pressures, as determined by the $12CO_2$ absorption measurement itself, in the sample and reference chambers are close to each other. When this point is reached, the pump is turned off, and the $13CO_2$ measurement is performed accurately in the knowledge that close conditions exist in the sample and reference 206 chambers. The condition of equal absorption is also monitored by means of an absolute 209 and a differential pressure measurement gauge 208. The pressure measurement is required to correct for changes in the extinction coefficient γ with pressure. As a result of these changes, the same absorption is obtained at different partial pressures. This procedure is likely to result in incorrect isotopic ratio measurements, unless an appropriate correction is applied, which has to be determined by control experiments.

Figure 20B:
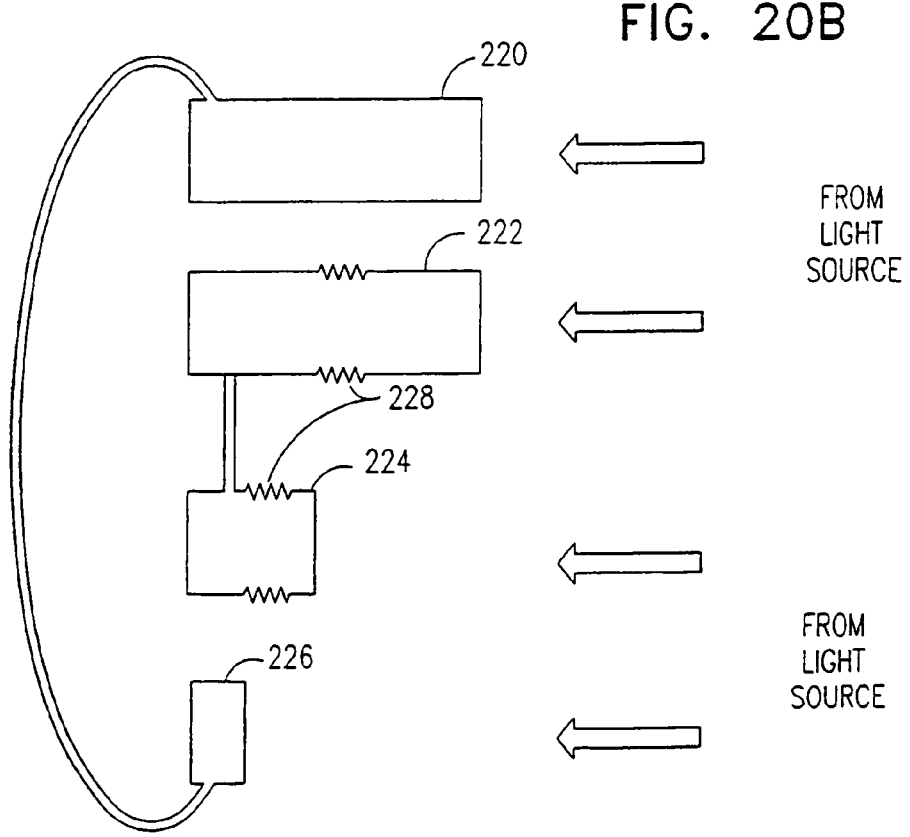
FIG. 20B schematically shows a method of equalizing the absorptions of sample and reference gases by changing chamber length.

A different approach to equalizing the absorption of the main isotope in the sample and reference gas can be accomplished by means of a change in the length of at least the reference or the sample chamber. This is shown in FIG. 20B which illustrates the sample chambers 222, 224 and reference chambers 220, 226 for each of the isotopes, with variable length configurations 228 added to the sample chambers for each isotope.

Figure 21:
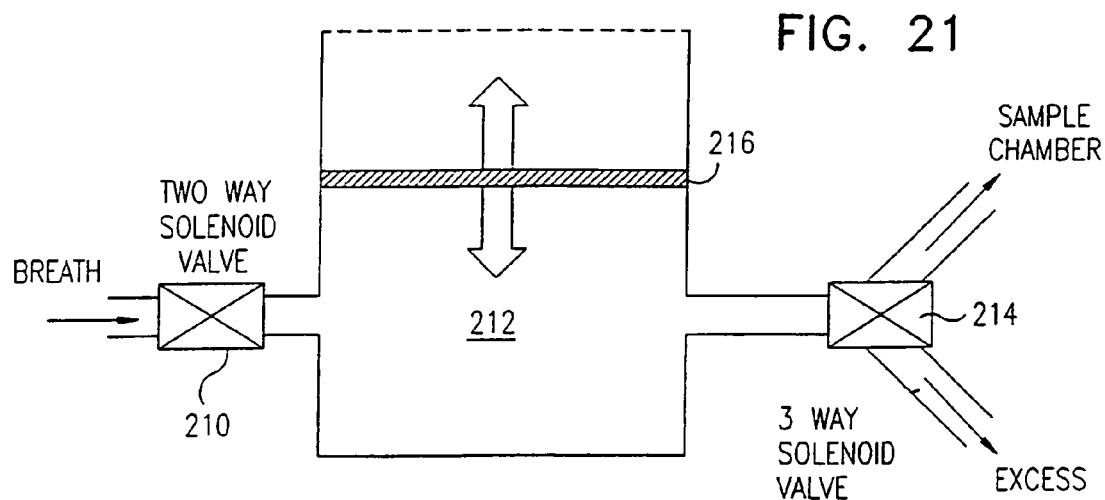
FIG. 21 illustrates how the pressure in the sample collection reservoir is maintained at a constant level while the sample gas is being accumulated or passed on after testing.

FIG. 21 shows the gas handling equipment used in a preferred embodiment of the present invention in order to ensure that the sample reservoir is maintained at a constant pressure while sample gas is being accumulated or pumped into the testing chamber. Entry of breath is permitted by opening of the one-way solenoid valve 210. The sample reservoir 212 is fitted with a piston 216, open on its other side to atmospheric pressure, such that the reservoir fills up naturally. At the exit from the reservoir, the two-way solenoid valve 214 is used to enable the accumulated sample to be pumped into the sample chamber. When this takes place, the piston falls, maintaining constant pressure in the vacated volume, such that no vacuum is formed.

The use of a reservoir in the embodiments shown in FIGS. 19 to 21, allows the analyzer to perform sampling of the exhaled breathes in such a way as to substantially increase the reliability of the measurement procedure. Firstly, it is known that exhaled breath follows a characteristic $CO_2$ wave front, whereby there is an initial steep rise in the $CO_2$ concentration of each exhaled breath, until a slowly rising plateau is reached. At the end of the breath, the volume falls rapidly again to a very low residual level. In order to ensure that the breath sampled is characteristic of the breath exhaled from the lungs, and not breath which has been standing in the oral or nasal passages, or has been reinhaled from a previous breath, it is important to sample breath only from the plateau region of the breath wave. This can be easily accomplished according to the embodiment described herein using a sampling reservoir, by means of valving which rejects the breath from the first and last part of each breath wave, and only samples breath from the plateau region. The detection of the exhalation can be performed optically by following changes in the optical absorption of the exhaled gas, or by monitoring changes in the exhalation dynamic pressure.

Furthermore, the use of such a sampling reservoir allows the analyzer to take an average of several breaths, instead of relying on a single breath sample, which could be atypical of the mean breath of the patient. The partial pressures of the various components of exhaled breath vary from breath to breath in a random manner, and averaging is therefore a very important procedure to ensure accurate measurements. The patient exhales a number of breaths freely into the reservoir. From the reservoir, the analyzer draws an averaged sample for measurement once measurement of the previous sample has been completed. This embodiment has a number of additional advantages. Firstly, the patient is non-functional in the sampling process, and simply breathes at his natural rate into the breath tube, or via a nasal cannula. The inlet valving of the analyzer ensures that the correct sample is taken for measurement. In addition, the breath is allowed to stand, which ensures good temperature and pressure conditioning with respect to the environment. Finally, the sampling from the reservoir is performed at an approximately fixed partial pressure, such that the measurement is less sensitive to environmental and lamp emission changes, and to cross sensitivity.

FIGS. 19 to 21 illustrate embodiments of reservoirs which provide a certain increase in the level of accuracy attainable in such instruments. In order to further increase the measurement accuracy, it is necessary to incorporate more advanced techniques, which will be described in the following preferred embodiments of the present invention.

Figure 22:
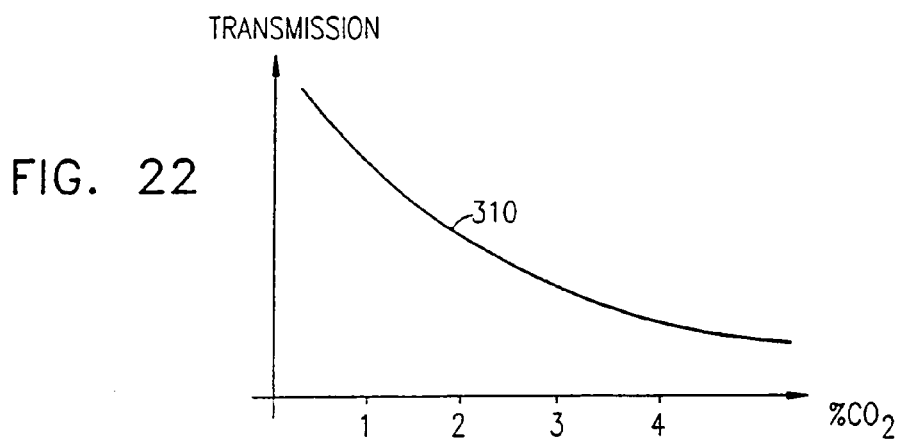
FIG. 22 shows a graph of the infra-red transmission of the $^{12}CO_2$ gas in the sample chamber as a function of its concentration.

Reference is now made to FIG. 22, which shows a graph of the infra-red transmission of the $^{12}CO_2$ gas in the sample chamber as a function of its concentration. This curve 310 is commonly called the "absorption curve", even though the abscissa shows the gas transmission. The curve has an exponential form, where the constant of the exponent, γ, varies somewhat with the environmental conditions of the gas itself.

In order to operate the analyzer at optimum sensitivity, the analysis cell length is selected to maximize the cell sensitivity, which is defined as the change in transmission per unit change in normalized gas concentration, as given by the expression:

$$\text{Sensitivity} = \frac{\Delta \text{Trans.}}{\Delta p[^{12}CO_2]/p[^{12}CO_2]} \quad (2)$$

where Δ Trans. is the change in transmission through the analysis cell arising when the partial pressure of the $^{12}$Carbon Dioxide $p[^{12}CO_2]$ changes by $\Delta p[^{12}CO_2]$.

Figure 23:
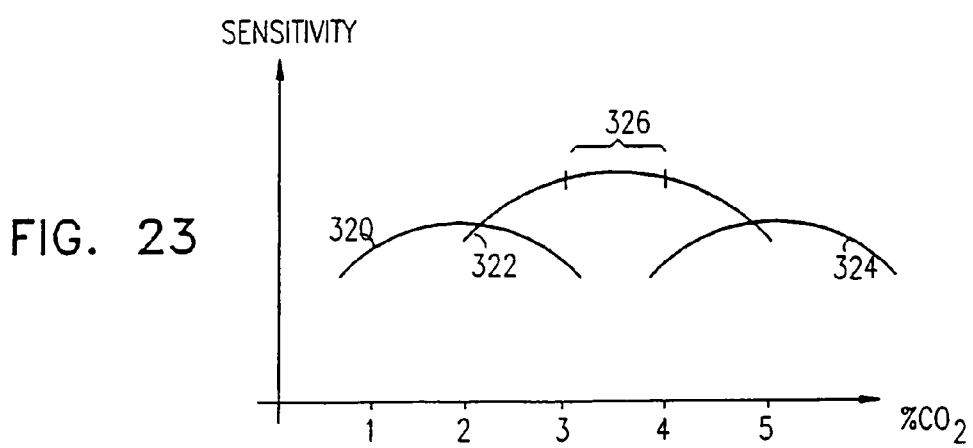
FIG. 23 shows the change in cell sensitivity as a function of concentration for analysis chambers with three different cell lengths.

FIG. 23 shows the change in cell sensitivity as a function of concentration for analysis chambers with three different cell lengths, marked 320, 322 and 324. A cell length is selected which provides maximum overall sensitivity together with minimum dependence of sensitivity on gas concentration in the region of the desired gas concentration of 3 to 4%. For the cell lengths shown in FIG. 23, the cell length shown by curve 322 is optimum, since at 3 to 4% concentration, it has a region of fairly constant sensitivity 326 at its maximum sensitivity.

Figure 24:
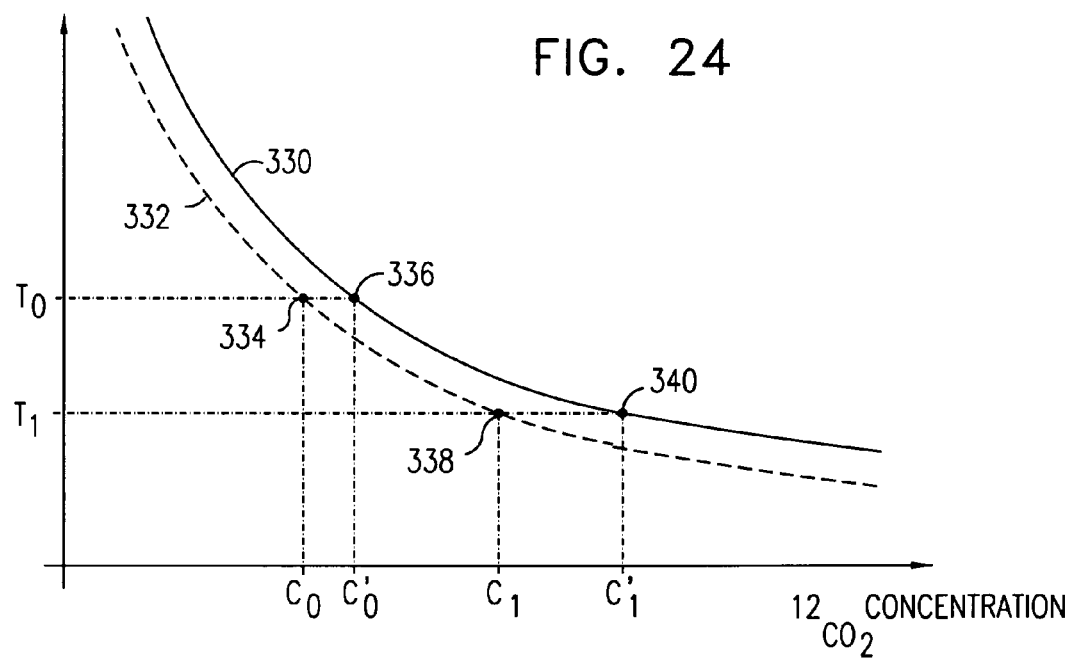
FIG. 24 is similar to the simple absorption curve shown in FIG. 22, but includes further detail to illustrate the problems which arise when absorption measurements are made at widely different partial pressures.

FIG. 24 is similar to the simple absorption curve shown in FIG. 22, but includes further detail to illustrate the problems which arise when absorption measurements are made at widely different partial pressures. The extinction coefficient, $\gamma$, which characterizes the absorption curve as defined by equation (1) in the background section, is not strictly a constant, but varies somewhat with such factors as the sample gas pressure and temperature, the excitation lamp gas pressure and temperature (if the gas analyzer uses an isotope-specific source lamp of the type described in U.S. Pat. No. 4,755,675), the ambient humidity, and cross sensitivity effects with other gases present in the sample.

As a result of these effects, the absorption curve 330, against which the spectrometer was calibrated when leaving the factory, is in fact incorrect for the conditions prevalent at the time the measurement is made, and the correct results should be given by curve 332. Thus, for a transmission measurement $T_0$, whereas the true concentration of $^{12}CO_2$, as given by the intersect point 334, should be $C_0$, the result shown on the instrument is $C_0'$, as given by the intersect point 336. By means of regular calibration procedures, it is possible to correct the readings for the difference in concentrations $C_0'-C_0$, by means of a simple correction algorithm factor, which is equivalent to shifting the curve back to its calibration position.

However, if a measurement is now performed at a different gas concentration, such that the transmission measured is $T_1$, since the slope of the absorption curve in the region of intercepts 338 and 340 is different, the concentration correction $C_1'-C_1$, is also different, and the correction made at the value $T_0$ is no longer valid. This illustrates the need to perform the absorption measurements on samples held at very closely controlled environmental conditions, this being one of the aims of the intermediate chamber of the present invention.

Even in simple embodiments of the present invention, wherein the isotopic ratio is measured directly by making absorption measurements on the sample gases only, without the use of a reference gas channel, the use of an intermediate chamber to ensure that all points measured are close in concentration to each other, enables higher accuracies to be achieved. Thus, for instance, if one breath having a 4% concentration of $^{12}CO_2$ is measured, followed by a breath with 5% of $^{12}CO_2$, meaning that the difference in percentage is 1%, and because of the "shift" of the absorption curve, the actual values obtained by the absorption measurement are say 4.3% and 5.5%, the apparent difference between the two concentration ratios is 1.2%, instead of 1%. If, on the other hand, because of the use of an intermediate chamber system, both measurements were made at concentrations close to each other, such as for instance 4% and 4.2%, the "shift" in the absorption curve caused by exactly the same external effects as the previous case, results in a change of the measured concentrations to say, 4.3% and 4.52%, i.e. the apparent difference between the two concentration ratios is 0.22%, instead of 0.2%. Thus, by making the measurements at concentrations close to one another, the effect of changes in the absorption curve on the measurement accuracy is much reduced.

In practice, the operating conditions of the spectrometer, such as measurement cell pressure and length, are chosen such that measurements are made in the region of points on the absorption curve such as 334, 336, rather than points such as 338, 340. Under these conditions, the sensitivity of the instrument to environmental changes in the absorption curve is lower, and at the same time, the absolute sensitivity of the transmission to changes in gas concentration is higher.

From these considerations, it is apparent that an accurate isotope concentration measurement can only be achieved when the measurement of each gas sample is performed under essentially identical conditions. The optimum $^{12}CO_2$ concentration for the $^{12}CO_2$ breath test, occurs at around 3%, though this value is somewhat dependent on the physiological characteristics of the patients, and on the atmospheric pressure externally. The function of the intermediate chamber according to a preferred embodiment of the present invention, is thus to generate from the breath samples inputted to the instrument, a supply of gas samples for analysis, each sample having a concentration of $^{12}CO_2$ as close as possible to the optimum.

Figure 25A:
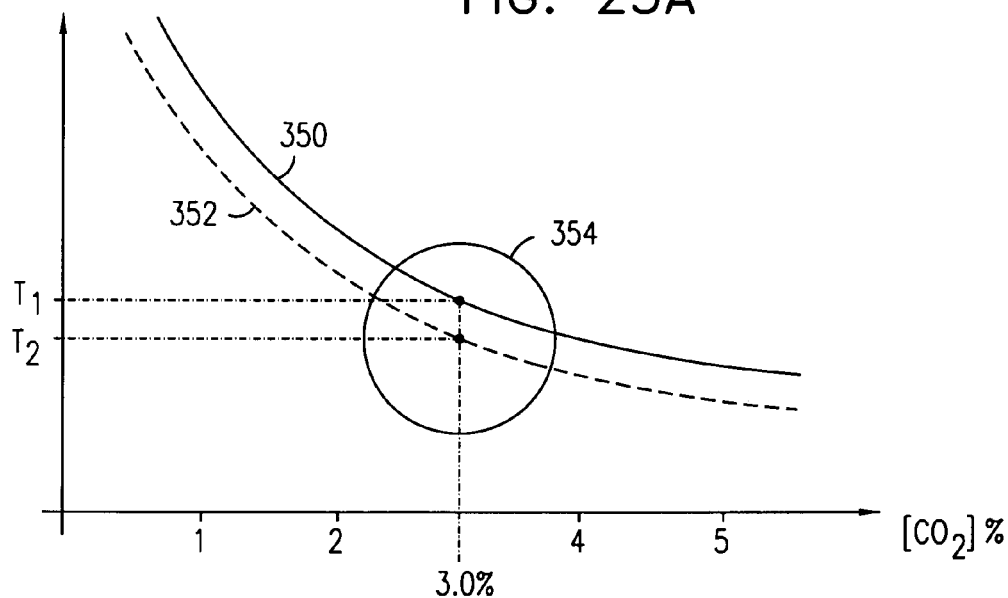
FIG. 25A shows the absorption curve for the gas in the reference cell, which contains a fixed and known percentage of the reference gas.
Figure 25B:
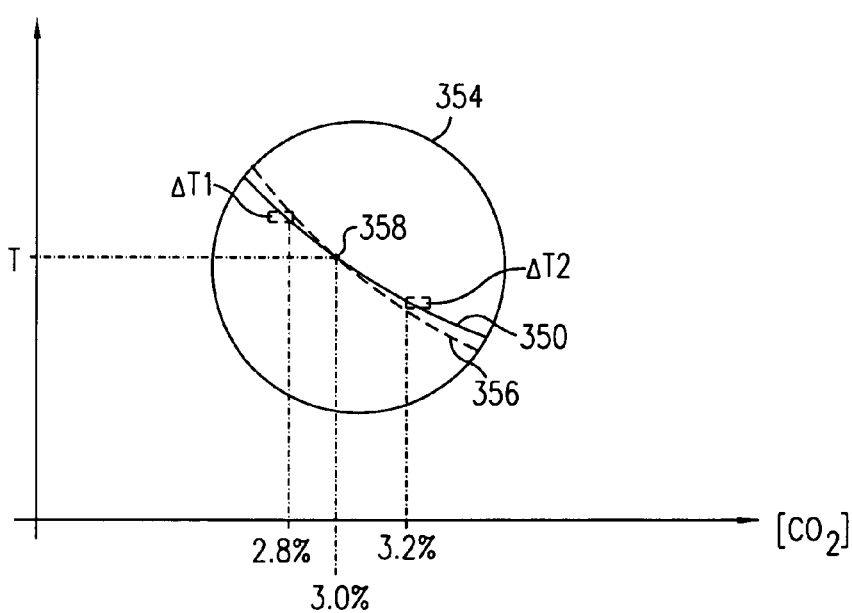
FIG. 25B shows an enlarged view of the area around the reference gas concentration point.

Reference is now made to FIG. 25A and FIG. 25B, which illustrate a correction mechanism used for increasing measurement accuracy, by constraining the operating conditions to remain in the region of what is known as the anchor point of the curve. In FIG. 25A, the absorption curve 350 shown is for the gas in the reference cell, which contains a fixed and known percentage of the reference gas, typically chosen in the region of 3%. At this point, the calibration of the instrument is such that a transmission level T1 is measured. Because of the above-mentioned environmental effects, this known concentration results in an actually measured transmission of T2. As explained above, the instrument uses a shifted absorption curve for calculating concentration, so that the readings in the region 3% of concentration are corrected by an amount (T1–T2). However, because the shape of the absorption curve is exponential, a linear shift of the whole curve parallel to the transmission axis only results in an accurate correction at the known concentration point, in this case 3%, and in its immediate vicinity 354, where the departure of the curve from linearity is minimal.

FIG. 25B shows an enlarged view of the area 354 around the reference gas concentration point, showing the original absorption curve 350 and the linearly shifted absorption curve 356. By maintaining the gas concentration close to this reference concentration, which is known as the anchor point of operation, the correction for environmental changes can be made very accurately. In the embodiment represented by the graph of FIG. 25B, a range of concentration of 2.8% to 3.2% is shown as the permitted region around the anchor point. At the anchor point itself 358, the transmission T is the exactly corrected value. At the two extremities of the chosen permitted region of operation shown, any transmission innaccuracy is limited to small corrections $\Delta T1$ and $\Delta T2$ respectively.

Figure 26:
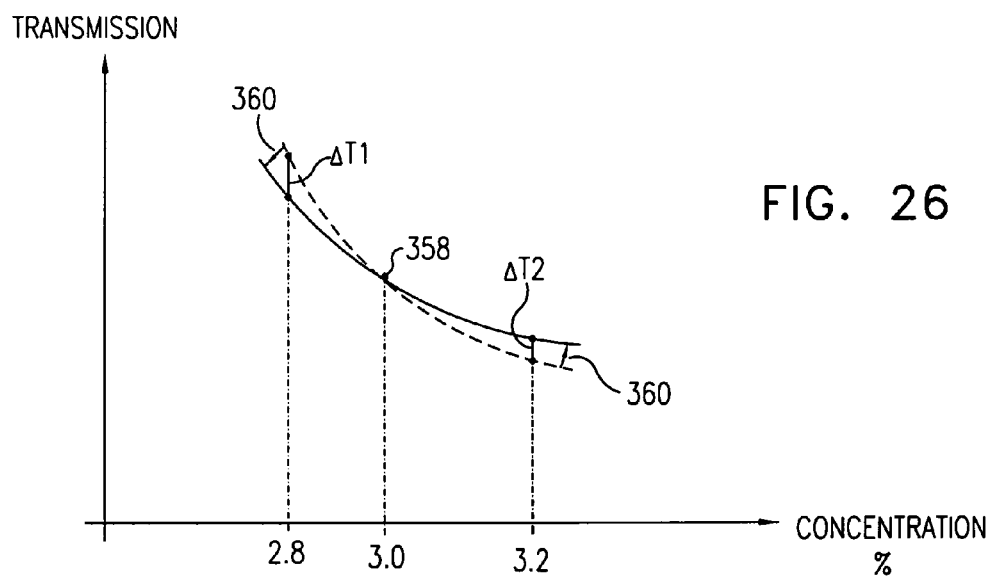
FIG. 26 shows an absorption curve correction known as skew correction.

Even after constraining operation to around the anchor point, a further correction may be performed on the reference gas absorption curve, known as skew correction. This correction is illustrated in FIG. 26. After applying the lateral shift correction to the absorption curve, skew correction introduces an angular rotation 360 to the curve around the anchor point 358, thereby almost completely eliminating the residual $\Delta T1$ and $\Delta T2$ inaccuracies arising from the small angular disparity between the corrected and original absorption curves.

Figure 27:
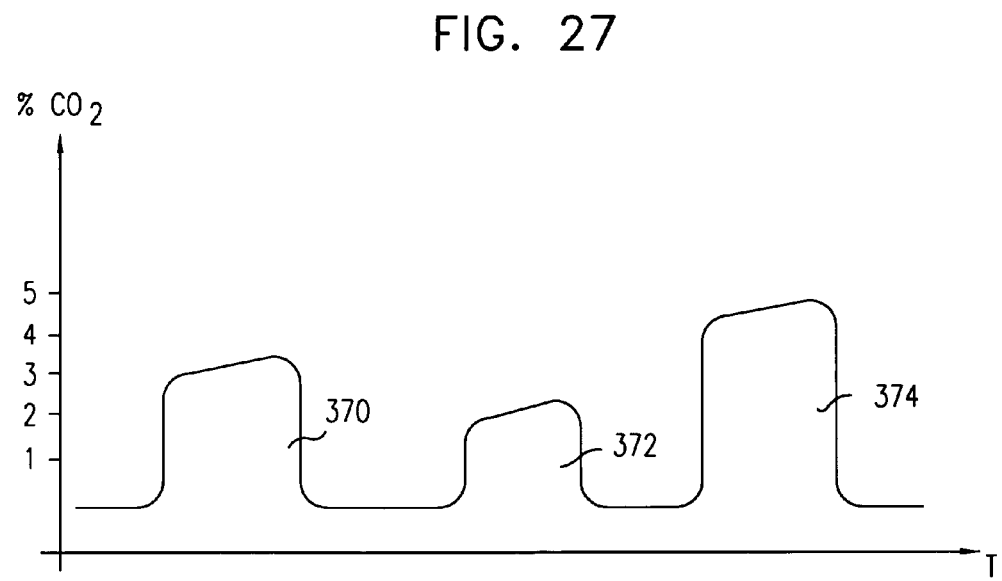
FIG. 27 shows a representation of a train of breaths, as exhaled from a patient.

Reference is now made to FIG. 27, which shows a representation of a train of breaths, as exhaled from a patient whose breath is to be tested in an isotopic gas analyzer according to the present invention. The figure shows how the percentage of carbon dioxide in the breath can vary from breath to breath as a function of time. In the representation shown, each breath has a different average $CO_2$ percentage concentration, where the term concentration is used to mean the average plateau concentration level. Thus, the first breath shown 370, has a concentration of 3% $CO_2$, the second one 372, has 1.5% and the third one 374, has 5%.

In the Applicants' previously described intermediate chamber implementation, as described in Israel Patent Application No. 121793, gas from the plateaus of the various breaths 370, 372, and 374 are simply collected in the so-called reservoir chamber, and an average value of the breath concentration used for the measurement. There are two main disadvantages to this simple averaging method:

a) There is a spread of concentration in the accumulated samples from one patient to the next.

b) Even for a single patient, his objective clinical condition can change during the course of the breath test, and this can cause changes in the concentration level from one accumulated sample to the next.

In another preferred embodiment of the present invention, the simple averaging function of the intermediate chamber is supplemented by the addition of pneumatic control elements, which perform two additional functions. Firstly, they determine which part or parts of each breath wave are to be accumulated in order to achieve the preferred accumulated sample gas concentration for optimum measurement sensitivity. Secondly, they perform the dilution of the accumulated sample gas, if found necessary, when the sample has a concentration above the optimum. As a result, a sample of very closely controlled concentration is obtained.

Figure 28:
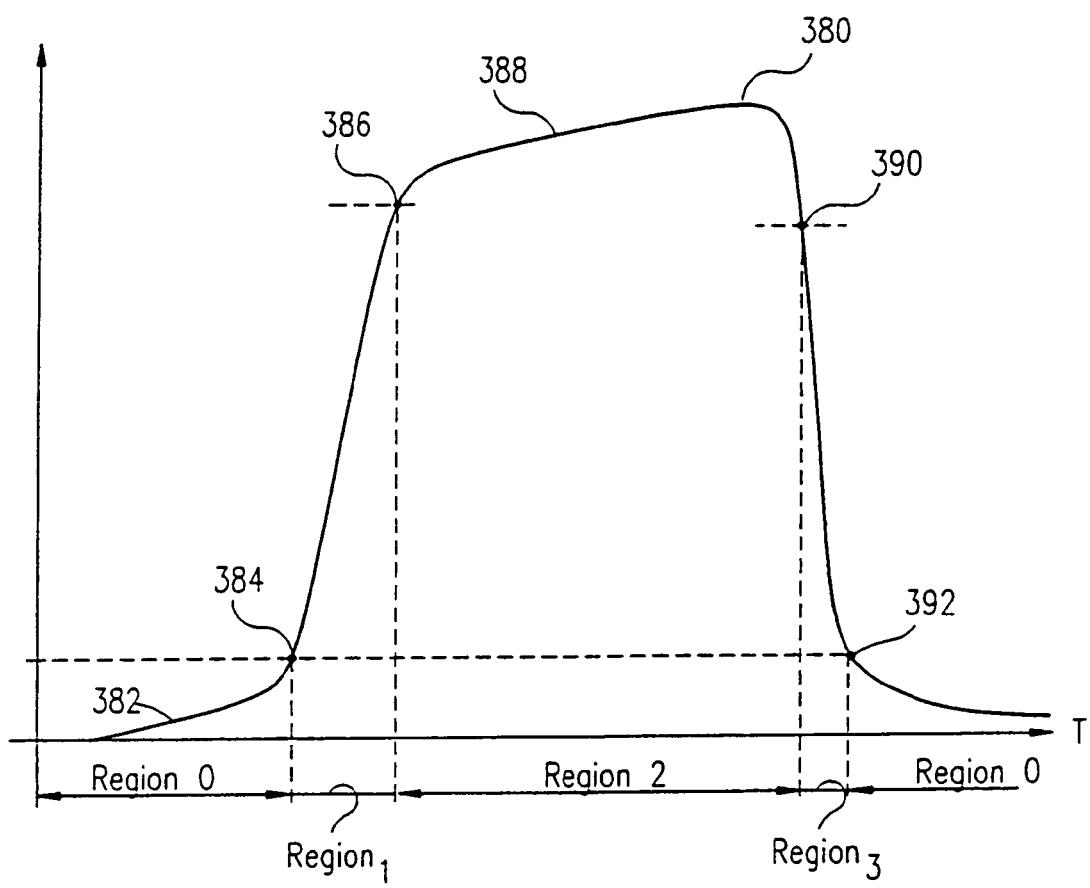
FIG. 28 shows a time plot of a typical breath wave with its constituent parts.

In order to describe this process, reference is now made to FIG. 28, which shows a time plot of a typical breath wave 380, with its constituent parts. The wave begins with a slow rise of the $CO_2$ signal to reference ratio 382, to the "threshold start" point 384, usually defined as the point at which the ratio reaches a level of 10%. This region is characterized by a very low level of $CO_2$, and it is therefore known as Region 0, or the baseline region. There then follows a slope with rapid rise of $CO_2$ content towards the plateau 388, terminating at a point known as the "threshold up" 386, when the $CO_2$ concentration ratio reaches 90%. This is known as Region 1. The time taken for this region is typically 50 to 100 msec. The plateau itself 388 is known as Region 2, and the slope from the "threshold down" point 390 to the "threshold end" point 392, is Region 3. Beyond the "threshold end" point, there is another baseline Region 0, bereft of $CO_2$ until the commencement of the next breath.

Figure 29:
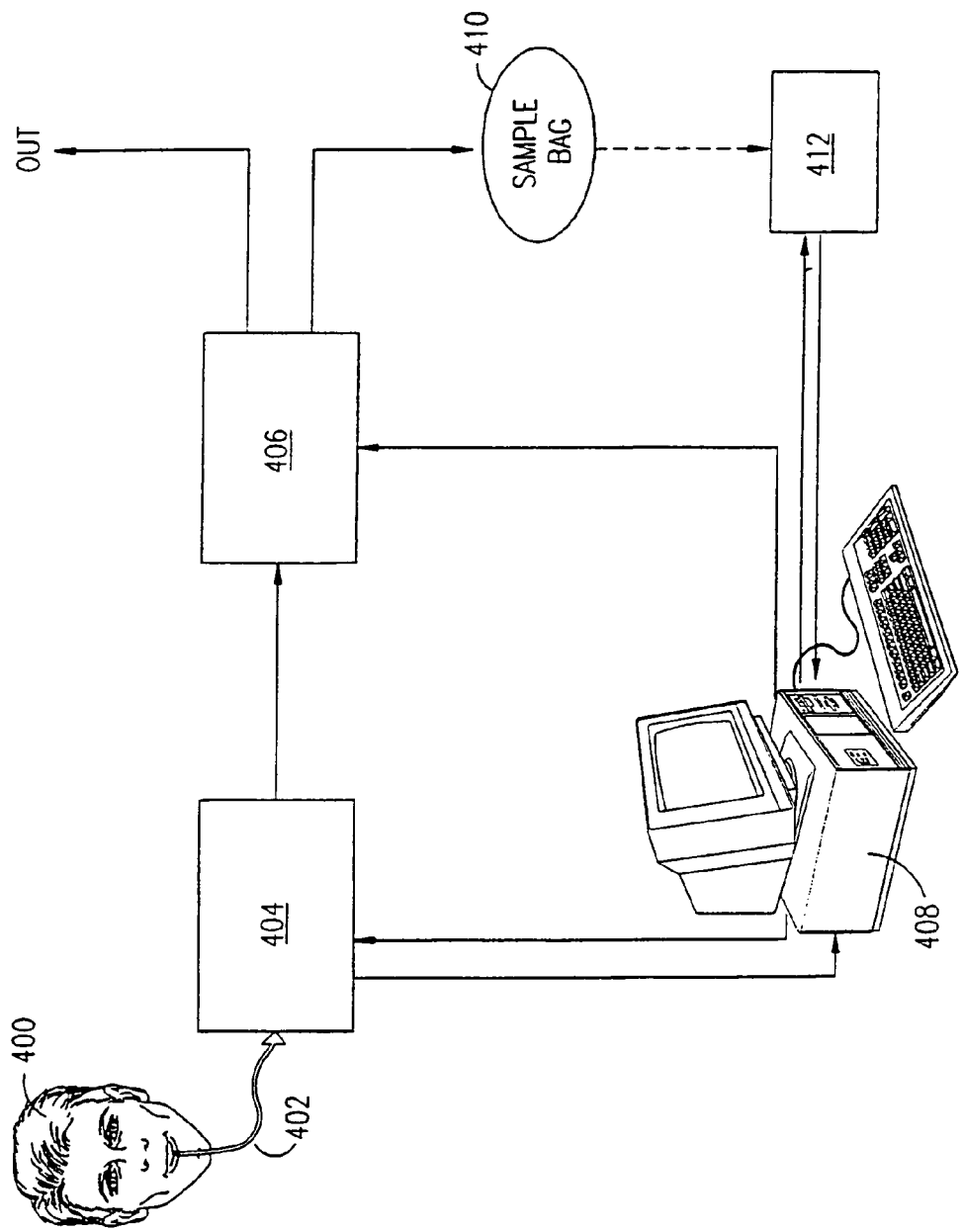
FIG. 29 is a schematic representation of a breath test system to illustrate the operation of an intermediate chamber system.

FIG. 29 is a schematic representation of a breath test system according to the present invention, to illustrate the operation of such an intermediate chamber system. The patient 400 undergoing the test breathes or blows into the nasal or oral cannula 402. The breath samples are inputted to a breath sensor module 404, whose function is to monitor the individual input sample breaths. A controlled two-way solenoid valve 406 is operative to direct the sample gas from the breath sensor module either into an accumulation bag 410, or if unneeded, out into the room area. From the sample bag, as soon as enough gas has been collected, and the concentration of the main isotope has reached and stabilized at the predetermined level, 3% in the case of the currently described preferred embodiment, the sample gas is passed periodically to the NDIR spectrometric measurement cell 412, for measurement of the ratio of $^{13}CO_2/^{12}CO_2$ in the sample tested. A computer 408 receives and processes the results of the measurements and of all the parameters measured in the system, and accordingly controls the operation of the whole intermediate chamber system. The breath sensor module contains a fast carbon dioxide probe for monitoring the wave of the breath inputted from the patient. The speed of this probe is such that it can differentiate between the different regions of the waveform shown in FIG. 28.

Figure 30:
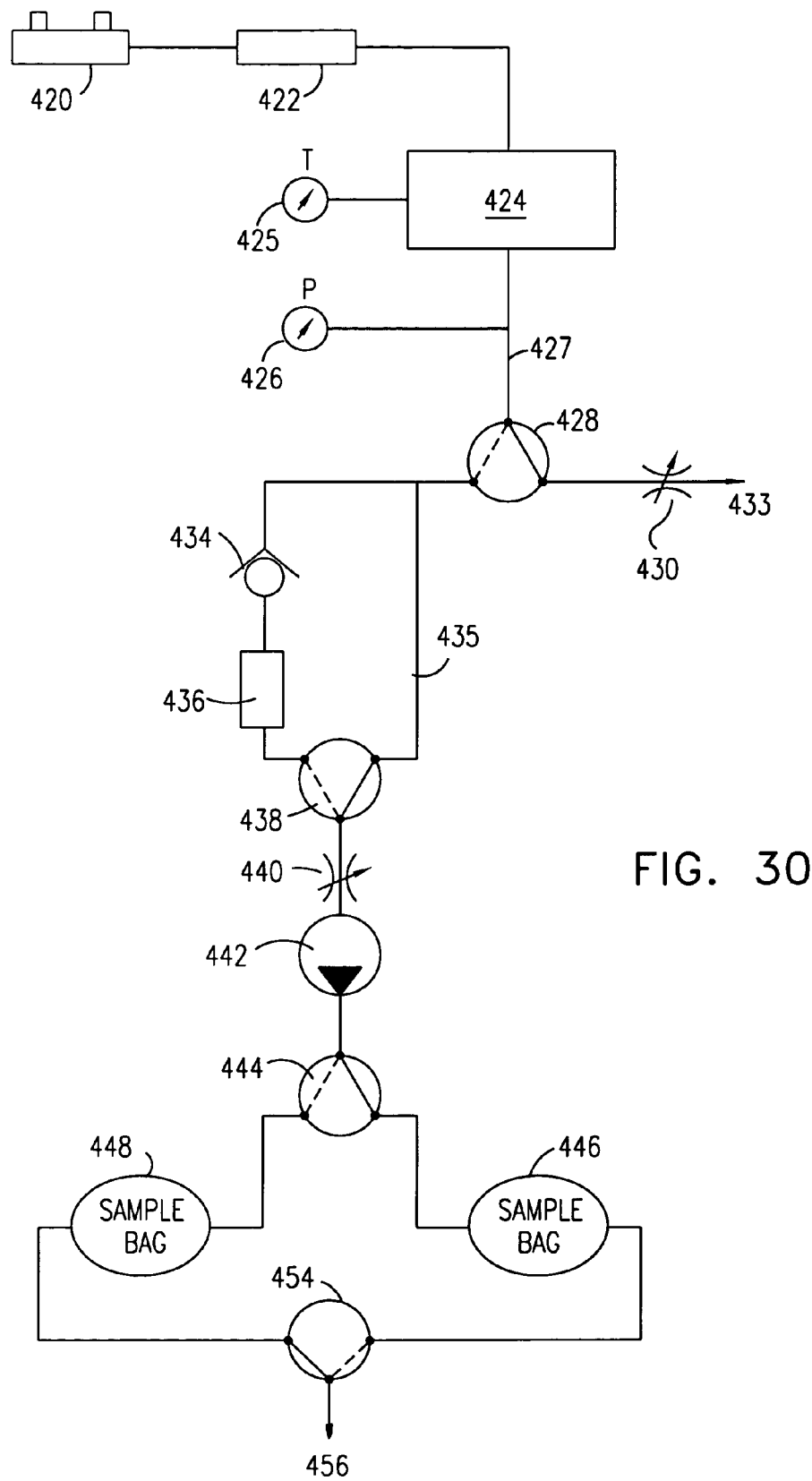
FIG. 30 illustrates a preferred embodiment of the gas handling system of a carbon dioxide breath test system based on an isotopic gas analyzer incorporating an intermediate chamber system.

Reference is now made to FIG. 30 which illustrates a preferred embodiment of the gas handling system of a carbon dioxide breath test system based on an isotopic gas analyzer incorporating an intermediate chamber system, constructed and operative according to the present invention. Samples of the breath of the subject are collected by means of the nasal cannula 420, though an oral breath collection tube could equally well be utilized for the purpose. The breaths are then passed through a filter line 422 to reduce moisture content. A fast $CO_2$ probe 424 is located immediately following the filter line, in order to dynamically monitor the carbon dioxide concentration in the breath waves inputted to the system. The response time of this $CO_2$ probe should be as short as possible, and according to a preferred embodiment of the present invention, is 50 msec. or less. The temperature and pressure of the inputted breath samples are measured by means of probes 425, 426, and the results used for applying environmental condition corrections to the absorption curve. The pressure monitor 426 also gives warning of system blockages.

The sample breaths then pass along a tube 427 of a predefined length to the two-way solenoid valve 428. This solenoid valve is the first decision-based operation performed on the breath samples, and it determines at what points in time the sample gas is allowed to continue into the system for accumulation and measurement, and at what points in time it is unneeded, and is ejected to the atmosphere. The decision and its timing are based on an estimate of the $^{12}CO_2$ concentration in the accumulated gas, as determined from the results of the previous accumulated points, and from the instantaneous level of $^{12}CO_2$ concentration in the breathwave passing, as determined by the dynamic $CO_2$ probe measurements. The criteria for this decision are discussed hereinunder, in conjunction with the software flow chart shown in FIG. 31. The tube 427 must not be shorter than a certain minimum length in order to provide decision time for the results of the $CO_2$ probe measurement to be received by the time the gas sample reaches the solenoid valve. The minimum tube length is determined by the flow speed of the gas sample and the response time of the $CO_2$ probe. At the same time, the tube should not be longer than necessary in order to avoid the possibility of missing collection of part of the gas because of flow rate dispersion. These two factors thus limit the tube length to an optimal defined length.

The ejected gas passes through a variable restrictor valve 430 and is then ejected into the atmosphere by means of an exhauster pump, or any alternative evacuation means 433. The sample gas passed by solenoid valve 428 into the system can proceed in one of two alternative paths, according to the setting of solenoid valve 438. In one path 435, the gas proceeds directly to the solenoid valve 438 without any processing. The gas in the second path traverses a check valve 434, to prevent reverse flow in that path, and then passes through a carbon dioxide scrubber 436, which effectively removes any $CO_2$ in the gas stream. If the breath test is being performed to detect isotopic ratios in an alternative gas, then the $CO_2$ scrubber 436 is replaced by an absorption unit specific for that alternative gas. The criteria for the decision as to the path into which the gas is directed by the solenoid valve, are discussed hereinunder, in conjunction with the flow chart shown in FIG. 31.

The selected gas is then drawn through the restrictor 440 by means of pump 442 to solenoid valve 444, for the next operative decision. The pump 442, together with evacuation means 433 in the ejection line, provide a flow of sample gas from the cannula, regardless as to whether a patient is attached or not. Even when attached, the pumps provide a flow regardless of how he breathes, or how he blows if connected to an oral sampling tube.

The existence of the positive suction effect afforded by pump 442 is the main reason for the location of the solenoid valve 438 at the exit of the scrubber path rather than at its entrance. If the valve were to be placed at the entrance to the scrubber path, then the suction of the pump 442 would continue to evacuate gas from the scrubber, whose volume may be comparatively large, even after the solenoid valve had changed direction to cut off flow through the scrubber. This would lead to inaccurate results. Location of the scrubber at the exit of the scrubber path ensures instant isolation of residual gas in the scrubber when the valve is switched over. Furthermore, the presence of the check valve 434, effectively isolates the scrubber at its input end, and prevents its contents from flowing back through the direct path 435 when the solenoid has cut off flow through the scrubber. An additional reason for the location of solenoid 138 is that the dead space and air mixing effects present therein would otherwise result in inaccuracies. Restrictor valves 430 and 440 are adjusted to ensure a steady and approximately equal flow of gas in both the sampling and the ejection paths. In this way, switching over of solenoid 428 does not disrupt the even gas flow in the system.

The two-way solenoid valve 444 is operative for alternating between gas collection in one sample bag 446 or the other 448. In this way, while the accumulated contents of one sample bag are being measured for isotopic ratio, the sample gas can continue to be collected in the second bag, thereby increasing the measurement rate of the instrument. The contents of each sample bag are allowed to flow via the two-way solenoid valve 454, to the isotope ratio measurement instrument 456. Solenoid valve 454 is operated in anti-phase to solenoid valve 444, such that when valve 444 is directing collected sample gas into bag 446, only the contents of bag 448 can be transferred for measurement, and vice versa.

Figure 31:
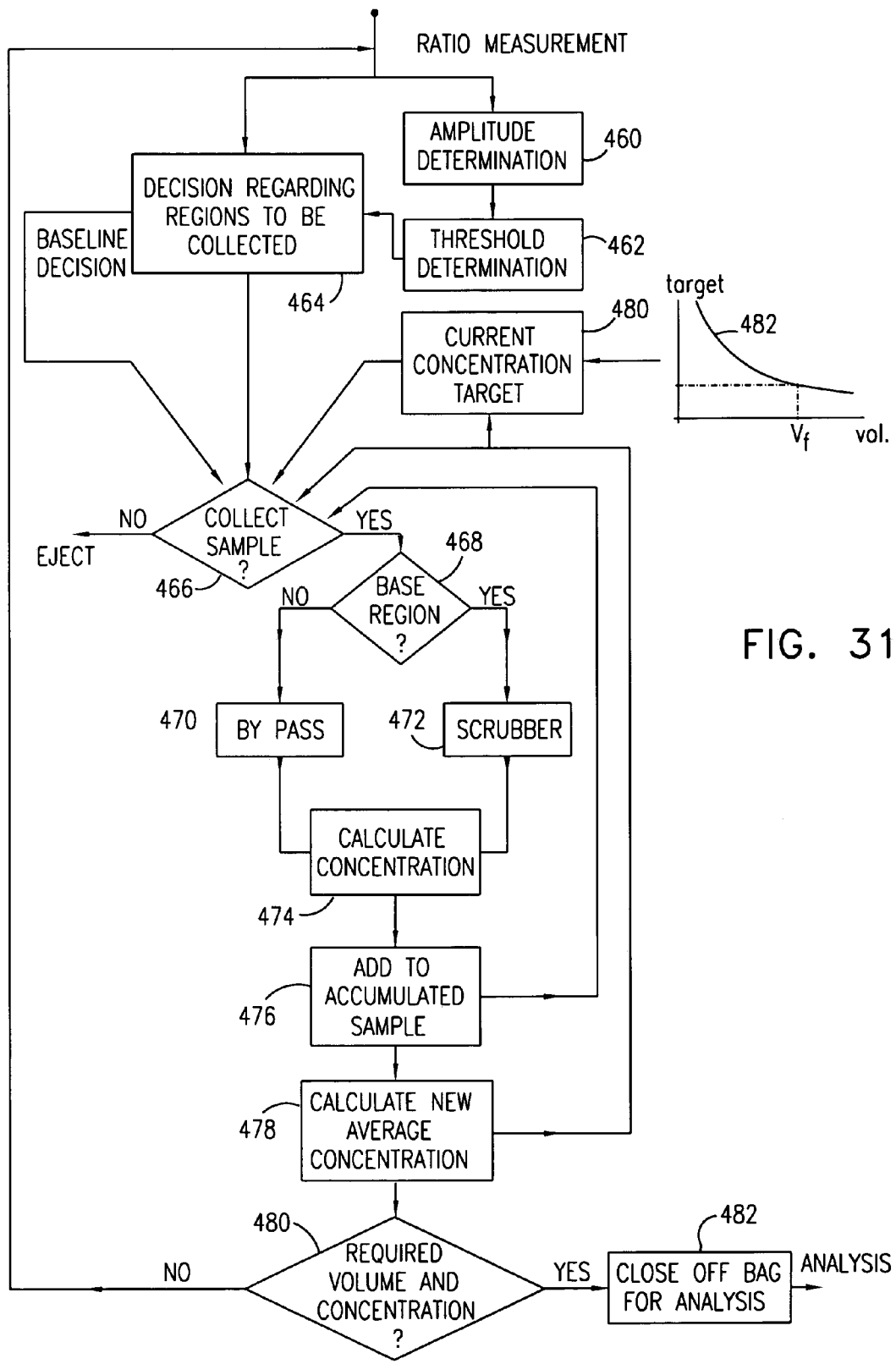
FIG. 31 shows the flow chart for the software controlling the dynamic sample collection process.

Reference is now made to FIG. 31, which shows the flow chart for the software controlling the dynamic sample collection process. This gas handling and preprocessing cycle is based on two initial assumptions regarding the collection procedure:

(a) Initially, while the volume of the sample bag is being filled, the whole of the breath wave plateau is collected from every breath, in order to provide the quickest accumulation of the required sample gas concentration, thereby increasing system sensitivity.

(b) The decisions as to what other parts of the breath wave are to be collected is dependent on the estimated concentration accumulated in the bag at the time of the measurement. As the bag is filling up, if it is apparent that the concentration of $CO_2$ in the gas collected from the plateau regions only is so high that the final collected volume will have a concentration above the target concentration—typically 3%—then a decision is made to collect gas also from the slope regions. The algorithm determines when the bag is full by a knowledge of the gas flow and the ratio measurement rate, typically once every 50 ms or 100 ms. This typically occurs after the accumulation of 150 gas measurement points, and if it is apparent that the concentration is still too high, then the gas in the bag is diluted by adding sample gas only from the baseline regions of the breath wave, after passing through the scrubber.

In the first step 460 shown in FIG. 31, the amplitude level of the plateau and the baseline are calculated, by checking back over the past accumulated points for the minimum and maximum amplitudes of the absorption points measured by the $CO_2$ probe. The amplitude is defined as the range between these maximum and minimum values, and the thresholds are determined in relation to this amplitude. A knowledge of the amplitude level is important in order to compensate for changes in the thresholds if changes in the breath pattern occur for any reason as the test proceeds. Once the amplitude range is known, the threshold levels for defining the different regions of each breath wave are calculated in step 462, and these defined levels are applied to each breath in step 464.

The decision taken in step 466, as to whether the sample should be collected or not, and if collected, which parts thereof, is dependent on a three inputted factors:

(a) The current target concentration in the intermediate chamber. At the commencement of the test, the target level is set at a high level, to ensure accumulation of maximum concentration, since if, when few breaths have been accumulated, it becomes apparent that the collected concentration is low, it is impossible to raise it thereafter, even if only plateau breath is collected thereafter. As the collection process proceeds, the target level is decreased towards the final desired concentration value by means of an iterative process, the rate of decrease being controlled by the number of "points" accumulated. This convergence from above is shown in the inset graph 482. The use of an iterative process which converges from above prevents a situation from arising wherein the concentration is still too low when the final volume has already been attained. Of course, if the patient is such that all or a majority of his breaths have a lower concentration than the target level, then this situation is unavoidable.

(b) The number of points accumulated, which is a measure of the volume of breaths accumulated.

(c) The concentration of the accumulated sample gas calculated from the average of all of the previous breaths accumulated in the bag.

At step 466, a decision based on these three inputs is taken, regarding the conditioning of the next sample breath. If the current concentration is higher than the target concentration, a decision is taken to collect gas also from the slope and even the baseline regions. If the current concentration is lower than the target concentration, gas is collected only from the plateau region, and gas from the other regions is ejected to the atmosphere. If the final volume of gas has already been collected, and the concentration is higher than the target concentration, only scrubbed gas from the baseline regions is collected, until the required dilution has been obtained.

A decision taken in step 466 regarding collection of gas only from the baseline regions, is executed in step 468. If, after filling the bag with the typically 150 points required to define a full bag, the decision is made at step 466 to dilute the bag contents, then at step 468, the decision is executed to pass the gas being collected through the scrubber path 472 to remove any residual $CO_2$ before adding to the accumulated gas, instead of being transferred directly through the bypass path 470.

At step 474, the concentration of $CO_2$ is calculated, and at step 476, the sample counter is increased by one point, to represent the last sample added to the bag. This counter is used to determine when 150 points have been added, which represents the full state of the sample bag undergoing the filling. The points added immediately after the opening of solenoid valve 428, and to a lesser extent 438, of FIG. 30 may be weighted, since, when a solenoid is switched, the gas flow is interrupted, and the flow rate may decrease temporarily. The first breaths collected after a solenoid valve switch are thus likely to be more dilute, and each point is given less weighting in the averaging calculation. This weighting is done both in the percentage concentration calculation and in the counter for estimating the volume of gas collected. Point weighting is also used if the pressure reading on the gauge 426 indicates that there is a reduction in flow, for instance because of a partial blockage.

The new concentration is calculated from the average of all the inputted breath samples after the addition of the last breath or parts thereof, and the concentration value updated, for use as a decision making input in step 466 regarding what part of the next sample to collect, and for updating the target concentration 480.

At step 480, the collected volume and concentration are checked, and if both have reached their target values, the collection process for that particular sample bag is terminated, and the bag is made available for analysis. If not, the process returns to step 460, and sample collection is continued.

The intermediate chamber system according to the present invention, incorporates an inherent self-calibration facility, without the need for operator intervention, which ensures continued accuracy for very long periods of use. The $CO_2$ probe measurement at the entrance to the system provides a measure of the $CO_2$ concentration, on the basis of which, the content of the bag at the end of the filling process is estimated. The accuracy of this measurement is dependent on a knowledge of the exact absorption curve, which may have changed because of operating conditions. This measurement can be compared with the integrated measurement of the isotopic ratio obtained from the complete gas analyzer system. The isotopic ratio measurement is highly accurate by virtue of the reference gas comparison measurement, and the other facilities built into the instrument. Any deviation of the two measurements can then be used to correct the absorption curve for the actual environmental conditions existent in the system. This is done by correcting the $CO_2$ probe calibration, so that the estimated bag concentration is made equal to the measured concentration.

There are a number of additional self calibration procedures which can be executed by virtue of the intermediate chamber facility according to the present invention. A sample with a comparatively high $CO_2$ concentration, for instance 5%, is collected from a subject, and the isotopic ratio is measured accurately in the gas analyzer. Next, the sample is diluted down using the intermediate chamber system to lower values, such as to 4.5%, 4%, 3.5% and so on. Each of these diluted samples is then also measured in the gas analyzer for isotopic ratio, and since each sample was derived from the same original breath sample, there should be no change in the isotopic ratio. Any change detected is indicative of a shift in the absorption curve, and the calibration can be adjusted accordingly to bring the readings back into agreement.

A further self-calibration facility is available, according to another preferred embodiment of the present invention, by observing the correlation of the spread of the isotopic ratio measurements obtained from negative subjects, with the $CO_2$ concentration measurements obtained from the same subjects. The procedure operates in the following manner. Breath samples are observed from a large range of negative subjects. In effect, the system can continually observe measurements obtained from negative patients to execute this procedure, and does not need any co-operation on the part of patients or staff. Each of these samples may have different levels of $CO_2$ concentration, and in this respect, the method is similar to the previous method described wherein a single sample is repeatedly diluted down in the intermediate chamber system to obtain multiple samples with different $CO_2$ concentrations. Each of these samples though, coming from a negative patient, should, within the noise limits of the measurements, have the same isotopic ratio, namely the patient's natural ratio. Therefore, if instead of finding constant isotopic ratios for all of the samples, any correlation is found between the isotopic ratios and the $CO_2$ concentrations measured, this is a sign of drift in the absorption curve, and lack of its correct calibration, or of any of the algorithms dealing with the calculations of the ratios. A correction can thus be applied to bring the instrument back into calibration.

This facility can be in operation all the time, and can therefore maintain a constant state of recalibration in the gas analyzer. Furthermore, it should be noted that this method can be applied to any gas analyzer, whether fitted with an intermediate chamber system or not.

The above preferred embodiments have illustrated the application of the intermediate chamber to advanced breath analyzers, for providing the ultimate accuracy and sensitivity achievable currently. In the ensuing FIG. 32 to FIG. 36 are shown simpler preferred embodiments of breath analyzers according to the present invention, using less sophisticated intermediate chamber systems. Such embodiments could be suitable for use as inexpensive point-of-care analyzers for widespread use, and the incorporation of the intermediate chamber systems according to these preferred embodiments of the present invention enable an increase in accuracy to be achieved also on these "low-end" instruments.

Figure 32:
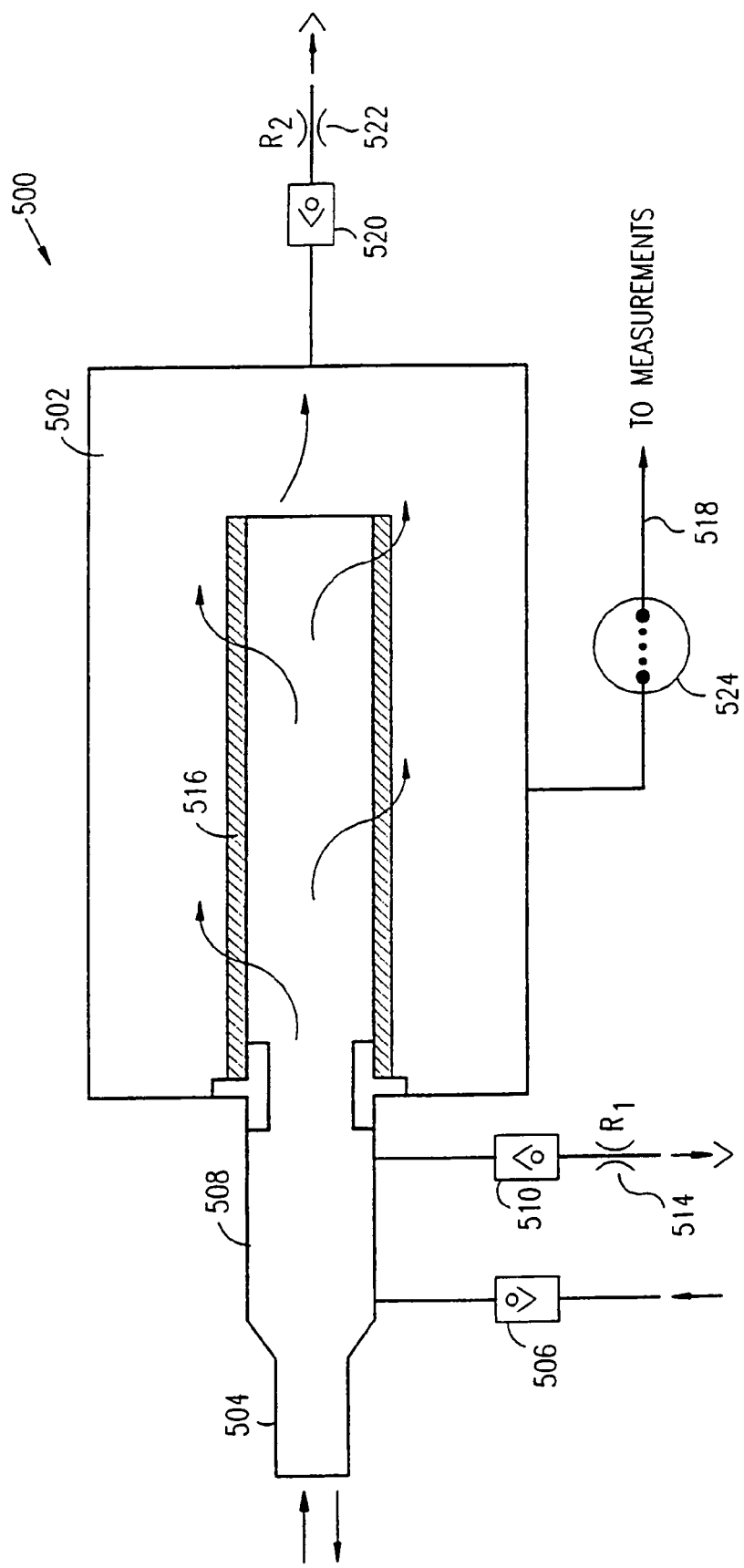
FIG. 32 to FIG. 34 show various preferred embodiments of a breath intake device incorporating mechanical check valve assemblies.
Figure 33:
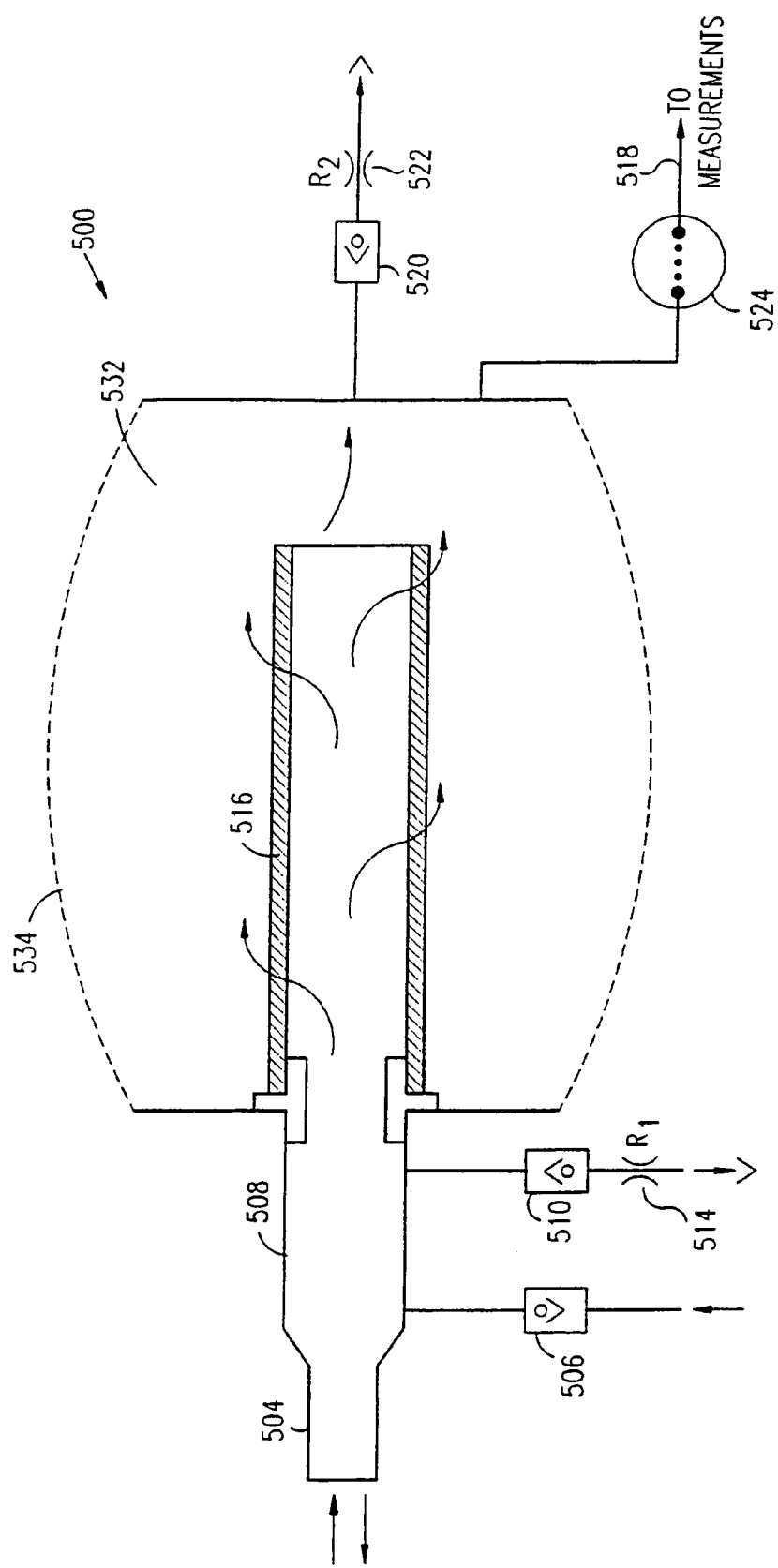
Figure 34:
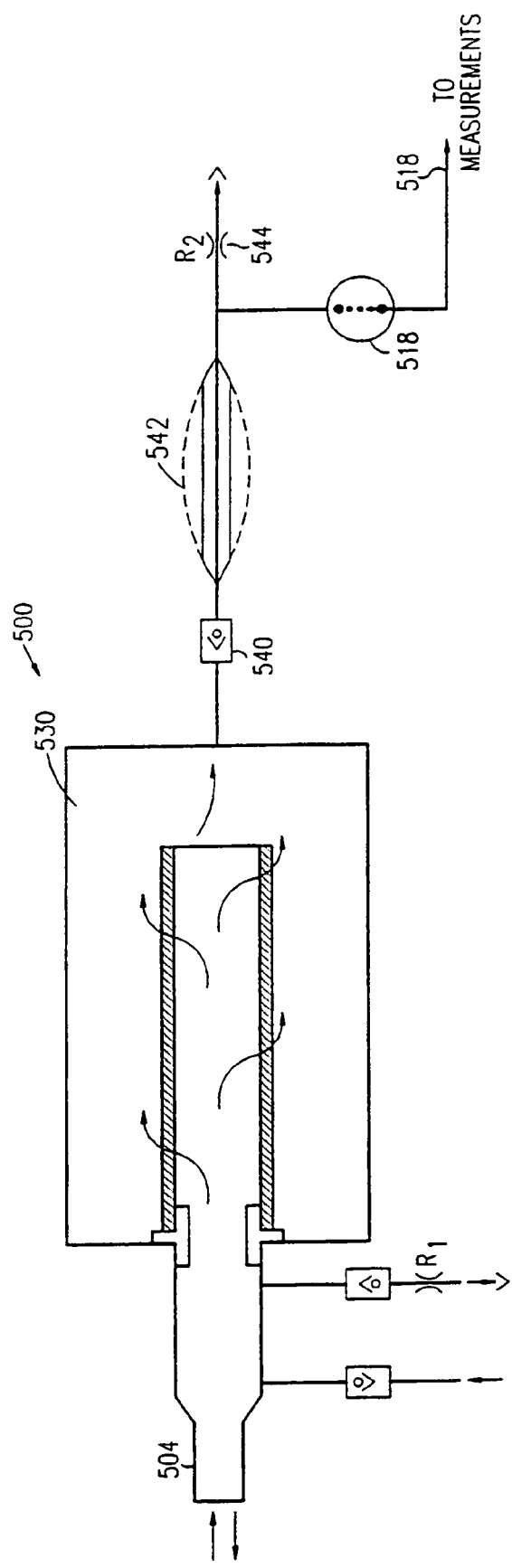

FIG. 32 to FIG. 34 show various preferred embodiments of a breath intake device incorporating mechanical check valve assemblies, which open at predetermined air flows such that preselected parts or all of a number of the patient's exhaled breaths are collected in the intermediate chamber.

FIG. 32 shows a mechanical check valve assembly 500 incorporating a reservoir with constant volume 502, for providing a constant sampling flow rate. The patient inserts the mouthpiece 504 into his mouth and breaths normally into the device. Inhaled air is sucked in through the check valve 506. Exhaled air passes into the body of the breath intake device, and closes the input check valve 506, so that the exhaled air is contained within the input chamber 508. This gas passes into the reservoir 502 through the filter element 516, whose function is to clean the air, to smooth out any pulsations arising from individual breaths, and to distribute the exhaled air throughout the whole of the outer volume 502. A restrictor valve R1 514 is used to set the level of gas flow permitted through the check valve 510. This outer part of the reservoir is fitted with a further check valve 520, which opens as soon as a slight overpressure indicates the presence of sample gas in the reservoir. A restrictor valve R2 522 is used to set the level of gas flow permitted through the check valve 520. The flow rate through R2 is much smaller than that through R1, such that most of the exhaled breath passes through R1 to the outside air, and only a small sample is passed into the reservoir on its way out through R2.

The ratio of restrictors R2/R1, known as N, the bypass ratio, determines the number of breaths required to fill the reservoir. Thus, for instance, for a reservoir of volume 50 ml, and an average resting patient with a breath volume of 500 ml, if a bypass ratio of 100 is chosen, then the volume of each breath which enters the reservoir is 500/N, which is 5 ml. Consequently, for this particular example, 10 breaths are required in order to replace the entire volume of the reservoir. The number of breaths collected can thus be chosen according to the patient and the test being performed, by selection of the ratio R21/R1. According to one preferred embodiment, when the reservoir volume has been filled by the determined number of breaths, the valve 524 is opened, and the sample accumulated in the reservoir from an average of the patient's breaths, is conveyed by means of tube 518 to the analyzer chamber for measurement. According to another preferred embodiment, valve 524 is open continuously, or is not even-present, and the device is used as a continuous breath monitoring system.

FIG. 33 shows another intermediate chamber breath sampling device, constructed and operated according to a further embodiment of the present invention. This mechanical check valve assembly 530 is similar to that shown in FIG. 32, except that it incorporates a reservoir with a variable volume 532, for providing a system for use with a variable sampling flow rate. The reservoir can be provided with flexible walls 534, which expand and contract during exhalation and inhalation. The other details of this embodiment are as marked in FIG. 32.

FIG. 34 shows a double reservoir intermediate chamber breath sampling device, constructed and operated according to a further embodiment of the present invention. This mechanical check valve assembly 530 is similar to that shown in FIG. 32, but the rigid reservoir has no outlet tube for conveying the accumulated averaged gas to the analyzing chamber. Instead, the reservoir output check valve 540 leads the accumulated gas into a second reservoir 542, which has flexible sides, like that in FIG. 33. The flow of gas into the second reservoir is controlled by the flow rate out of the second reservoir through the restrictor R2 544. When the second reservoir is full, its accumulated gas is outputted to the analyzing chamber by opening valve 518, as in the previous embodiments. The advantages of this double reservoir system are that firstly, it is possible to use standard disposable collection bags as the main collection reservoir, and secondly, the main reservoir can be installed in the instrument, away from the patient, so that the patient interface device becomes much more compact.

Figure 35:
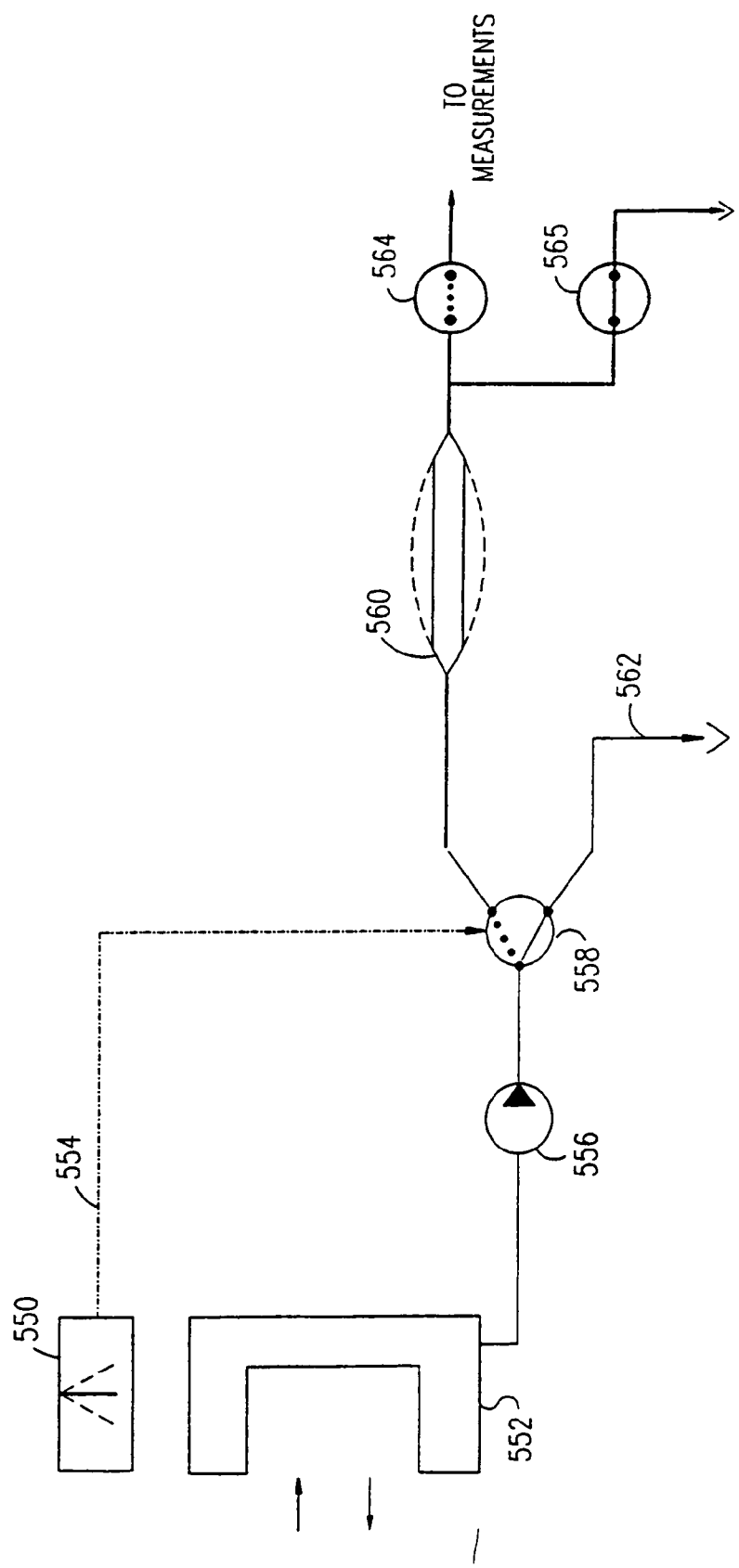
FIG. 35 shows another intermediate chamber breath sampling device, suitable for use with nasal cannula breath sampling, and uses a flow direction sensor, such as a piezoelectric membrane sensor, a strain gauge sensor, or a similar flow direction sensor.

FIG. 35 shows yet another intermediate chamber breath sampling device, constructed and operated according to a further embodiment of the present invention. This embodiment is suitable for use with nasal cannula breath sampling, and uses a flow direction sensor, such as a piezoelectric membrane sensor, or a strain gauge sensor, or a similar flow direction sensor. Such sensors are very sensitive, and can thus detect very slight breath flows, such as are common in pediatric cannula sampling. The flow direction sensor 550 is mounted on or near the nasal cannula intakes 552, and provides an AC electronic signal 554 proportional to the flow rate of the exhaled breath. The sampled breath from the cannula is drawn by means of pump 556 to switchable solenoid 558. The position of this solenoid is controlled by the signal from the flow direction sensor. So long as no appreciable exhalation flow is detected, the gas flowing down the line from the cannula is ejected into the room area 562. As soon as the flow sensor detects the flow of an exhaled breath, corresponding to the rise of the breath wave towards the plateau, the solenoid is switched such that the ensuing breath is directed into the intermediate chamber 560, for accumulation. When the breath wave passes, the gas from the cannula is again rejected, until the rise of the next breath wavefront. In this way, the intermediate chamber is used to accumulate breath only from the plateau areas of the exhaled breath, ensuring a high $CO_2$ concentration. When sufficient breaths have been collected in the intermediate chamber, solenoid 564 is switched, thereby allowing the collected breath sample to flow to the analysis chamber of the instrument for measurement. Solenoid 565 is used in order to vent the reservoir 560 speedily when necessary, by contracting its flexible walls with the solenoid valve 565 open to the atmosphere.

Figure 36:
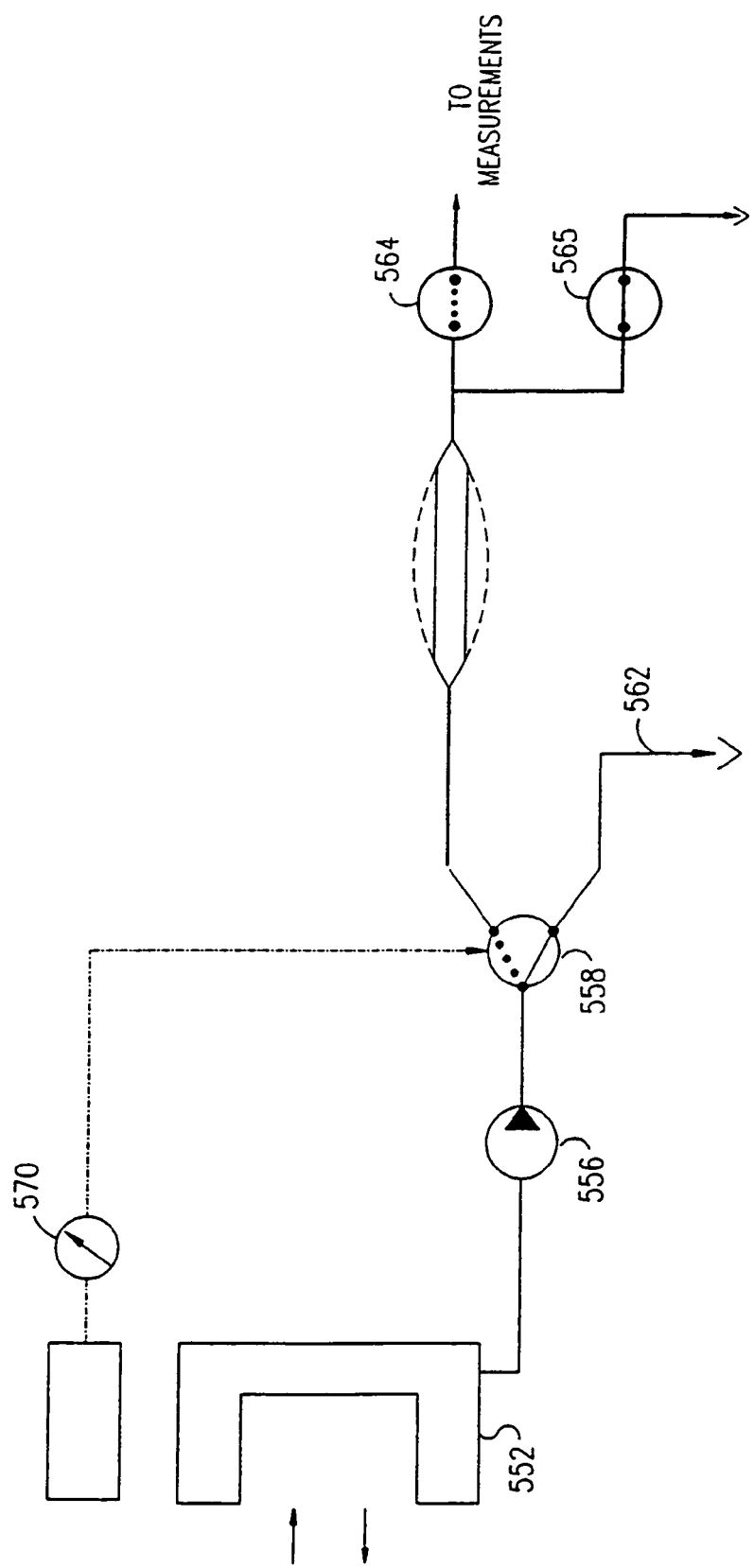
FIG. 36 shows another intermediate chamber breath sampling device, also suitable for use with nasal cannula breath sampling, which uses a differential pressure sensor, such as a thermoanemometer.

FIG. 36 shows another intermediate chamber breath sampling device, constructed and operated according to a further embodiment of the present invention. This embodiment, like that shown in FIG. 35, is also suitable for use with nasal cannula breath sampling, but it differs in that instead of using a sensitive flow direction sensor to detect the rise of the breath wave, this embodiment uses a differential pressure sensor, such as a thermoanemometer. The component parts of the intermediate chamber system are identical to those in FIG. 35, except that the control signal to the breath sampling solenoid 558 is provided by a differential pressure sensor 570, which detects the slight changes which occur in nasal cannula flow as the patient breathes. There are a number of advantages of using a true flow rate sensor, as enabled by the use of the differential pressure sensor of this embodiment, as compared with a flow direction sensor. Firstly, the electrical signal is more stable, especially for high or non-stable respiration rate applications, such as for neo-natal use. Secondly, it is possible to define the parts of the breath wave more exactly, and to select specific parts of the exhaled breath samples for accumulation in the intermediate chamber system. Finally, the use of a differential pressure sensor enables the comparatively more costly sensor measurement element to be separated from the breath sensing element. The sensor element can thus be installed in the instrument itself, and be connected to the patient by means of a cheap disposable sampling tube attached to the nasal cannula.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An isotopic gas analyzer for determining the ratio of at least a first and a second isotopic component of a gas, comprising:

at least one wavelength-stable source of radiation of wavelengths characteristic of at least one of said at least first and second isotopic components;

at least a first sample chamber comprising a first sample of said gas to be analyzed;

at least a first reference chamber containing a reference gas comprising said first and second isotopic components;

at least a second sample chamber comprising a second sample of said gas to be analyzed;

at least a second reference chamber containing a reference gas comprising said first and second isotopic components; and at least one detector detecting transmission through said at least first sample chamber and transmission through said at least first reference chamber, of radiation of wavelengths characteristic of said first isotopic component of said gas, and transmission through said at least second sample chamber and transmission through said at least second reference chamber, of radiation of wavelengths characteristic of said second isotopic component of said gas.

2. An isotopic gas analyzer according to claim 1, and wherein said at least one detector is a single detector.

3. An isotopic gas analyzer according to claim 2, and wherein said single detector detects said transmission through said chambers simultaneously at wavelengths characteristic of said first isotopic component of said gas, and of said second isotopic component of said gas.

4. An isotopic gas analyzer according to claim 2, and wherein said at least one wavelength-stable source of radiation comprises at least two wavelength-stable sources of radiation, each of wavelengths characteristic of one isotopic component of said gas.

5. An isotopic gas analyzer according to claim 4, said at least two wavelength-stable sources of radiation operating with respective at least first and second different timing characteristics, said analyzer also comprising a detection differentiator receiving an output from said at least one detector and distinguishing outputs corresponding to said at least two wavelength-stable sources on the basis of said first and second different timing characteristics.

6. An isotopic gas analyzer according to claim 5 and also comprising a second detector, wherein said single detector views absorption signal outputs from said at least two wavelength-stable sources and said second detector views zero calibration signals from said at least two wavelength-stable sources.

7. An isotopic gas analyzer according to claim 2, and wherein said at least one wavelength-stable source of radiation is one wavelength-stable source of wavelengths characteristic of at least said first and second isotopic components.

8. An isotopic gas analyzer according to claim 2, and wherein said at least one wavelength-stable source is at least one gas discharge lamp.

9. An isotopic gas analyzer according to claim 2 and wherein at least one of the environmental conditions of at least one of said samples of said gas and said reference gas are the same.

10. An isotopic gas analyzer according to claim 2 and also comprising osmotic means for achieving substantially the same isotopic concentration in said sample of gas and said reference gas.

11. An isotopic gas analyzer according to claim 2 and also comprising pumping means for achieving substantially the same isotopic concentration in said sample of gas and said reference gas.

12. An isotopic gas analyzer according to claim 2, and also comprising mechanical means for changing the length of at least one of said sample chambers and reference chambers for achieving substantially the same isotopic absorption in said sample of gas and said reference gas.

13. An isotopic gas analyzer according to claim 2 and wherein said analyzed gas is exhaled breath.

14. An isotopic gas analyzer according to claim 2 and also comprising a beam homogenizer to compensate for inhomogeneity in an optical path.

15. An isotopic gas analyzer according to claim 2 and wherein the spectral ranges of said at least first and second isotopic components are non-overlapping.

16. An isotopic gas analyzer according to claim 2 and wherein said sample chambers are interconnected pneumatically.

17. An isotopic gas analyzer according to claim 2 and wherein said reference chambers are interconnected pneumatically.

18. An isotopic gas analyzer according to claim 2 and wherein said sample chambers are connected thermally.

19. An isotopic gas analyzer according to claim 2 and wherein said reference chambers are connected thermally.

20. An isotopic gas analyzer according to claim 2 and wherein said first and said second isotopic components of said gas have a region of spectral overlap, and also comprising a system for lowering the pressure of said sample of gas, such that an absorption measurement in said region of spectral overlap is performed under conditions of lowered sample gas pressure.

21. An isotopic gas analyzer according to claim 1, and wherein said at least one detector detects said transmission through said chambers simultaneously at wavelengths characteristic of said first isotopic component of said gas, and of said second isotopic component of said gas.

22. An isotopic gas analyzer according to claim 1, and wherein said at least one wavelength-stable source of radiation comprises at least two wavelength-stable sources of radiation, each of wavelengths characteristic of one isotopic component of said gas.

23. An isotopic gas analyzer according to claim 22, and wherein said at least two wavelength-stable sources are gas discharge lamps.

24. An isotopic gas analyzer according to claim 22 and wherein said at least two wavelength-stable sources of radiation operate with respective at least first and second different timing characteristics, said analyzer also comprising a detection differentiator receiving an output from said at least one detector and distinguishing outputs corresponding to said at least at least two wavelength-stable sources on the basis of said first and second different timing characteristics.

25. An isotopic gas analyzer according to claim 24 and wherein said at least first and second different timing characteristics are first and second frequencies.

26. An isotopic gas analyzer according to claim 24 and wherein said at least first and second different timing characteristics are first and second phases.

27. An isotopic gas analyzer according to claim 24 and wherein said at least one detector is a single detector viewing outputs of said at least two wavelength-stable sources.

28. An isotopic gas analyzer according to claim 24 and wherein said at least one detector comprises two detectors, each viewing one of said at least two wavelength-stable sources of radiation.

29. An isotopic gas analyzer according to claim 24 and wherein said at least one detector comprises two detectors, and wherein one of said two detectors views absorption signal outputs from said at least two wavelength-stable sources and the other of said two detectors views zero calibration signals from said at least two wavelength-stable sources.

30. An isotopic gas analyzer according to claim 24 and wherein said detection differentiator comprises first and second synchronized signal processors.

31. An isotopic gas analyzer according to claim 1, and wherein said at least one wavelength-stable source of radiation is one wavelength-stable source of wavelengths characteristic of at least said first and second isotopic components.

32. An isotopic gas analyzer according to claim 31, and wherein said at least one wavelength-stable source is at least one gas discharge lamp.

33. An isotopic gas analyzer according to claim 1, and wherein said at least one wavelength-stable source is at least one gas discharge lamp.

34. An isotopic gas analyzer according to claim 33, and wherein said at least one gas discharge lamp is a single gas discharge lamp containing at least a first and a second excitation gas.

35. An isotopic gas analyzer according to claim 34, and also comprising:
at least first and second filters, each corresponding to a part of respective first and second spectra of said at least first and second excitation gas, said filters being interposed between said at least one wavelength-stable source of radiation and said at least one detector; and
a detection differentiator cooperating with said detector for distinguishing detector outputs corresponding to said first and second spectra.

36. An isotopic gas analyzer according to claim 35, and wherein said detection differentiator comprises at least one light valve modulating light passing through at least one of said first and second filters, in accordance with a known timing sequence.

37. An isotopic gas analyzer according to claim 36 and wherein said light valve is a chopper.

38. An isotopic gas analyzer according to claim 36 and wherein said light valve is a spatial light modulator.

39. An isotopic gas analyzer according to claim 36 and wherein said at least one light valve is operated with respective first and second different timing characteristics, and wherein said detection differentiator also comprises a detector output discriminator receiving an output from said detector and distinguishing outputs corresponding to said first and second excitation gases on the basis of said first and second different timing characteristics.

40. An isotopic gas analyzer according to claim 39 and wherein said first and second different timing characteristics are first and second frequencies.

41. An isotopic gas analyzer according to claim 40 and wherein said first and second different timing characteristics are first and second phases.

42. An isotopic gas analyzer according to claim 40 and wherein said detection differentiator comprises first and second synchronized signal processors.

43. An isotopic gas analyzer according to claim 36, and also comprising a zero calibration channel, and wherein said light modulation is also operative to modulate light transmitted through at least one of said sample chambers, reference chambers and said zero calibration channel.

44. An isotopic gas analyzer according to claim 34, and wherein said first and second excitation gases are isotopically labeled.

45. An isotopic gas analyzer according to claim 34, and wherein said filters are at least one of optical and gaseous filters.

46. An isotopic gas analyzer according to claim 34, and wherein said at least first and second excitation gases having overlapping spectral ranges including at least some interdigitated spectral lines; and also comprising a gas contents indicator receiving an output from said at least one detector and employing information detected by said at least one detector from at least two of said at least some interdigitated spectral lines.

47. An isotopic gas analyzer according to claim 46 and wherein said gas to be analyzed is maintained at a pressure below atmospheric pressure.

48. An isotopic gas analyzer according to claim 46 and also comprising filters to isolate non overlapping spectral ranges including at least some interdigitated spectral lines.

49. An isotopic gas analyzer according to claim 33, and wherein said at least one gas discharge lamp is two gas discharge lamps, containing respectively a first and a second excitation gas.

50. An isotopic gas analyzer according to claim 1, and wherein said at least one wavelength-stable source comprises at least one filter to define said wavelengths characteristic of at least one of said first and second isotopic components.

51. An isotopic gas analyzer according to claim 1 and wherein at least one of the environmental conditions of at least one of said samples of said gas and said reference gas are the same.

52. An isotopic gas analyzer according to claim 51 and wherein said reference gas comprises at least part of a sample of said gas.

53. An isotopic gas analyzer according to claim 51 and wherein said reference gas is a mixture containing at least one of said isotopic components at a known pressure and concentration.

54. An isotopic gas analyzer according to claim 1 and wherein said first sample of said gas and said second sample of said gas have essentially the same composition.

55. An isotopic gas analyzer according to claim 1 and also comprising osmotic means for achieving substantially the same isotopic concentration in said sample of gas and said reference gas.

56. An isotopic gas analyzer according to claim 1 and also comprising pumping means for achieving substantially the same isotopic concentration in said sample of gas and said reference gas.

57. An isotopic gas analyzer according to claim 1, and also comprising mechanical means for changing the length of at least one of said sample chambers and reference chambers for achieving substantially the same isotopic absorption in said sample of gas and said reference gas.

58. An isotopic gas analyzer according to claim 1 and wherein said analyzed gas is exhaled breath.

59. An isotopic gas analyzer according to claim 58 and wherein said exhaled breath is continuously sampled by use of a connecting nasal cannula.

60. An isotopic gas analyzer according to claim 58 and wherein said exhaled breath is continuously sampled by use of a breathing tube.

61. An isotopic gas analyzer according to claim 58 and wherein only a selected part of said exhaled breath is used for said analyzing.

62. An isotopic gas analyzer according to claim 1 and also comprising a beam homogenizer to compensate for inhomogeneity in an optical path.

63. An isotopic gas analyzer according to claim 1 and wherein the spectral ranges of said at least first and second isotopic components are non-overlapping.

64. An isotopic gas analyzer according to claim 1 and also comprising a zero calibration channel and an array of detectors, said array of detectors monitoring at least one of said sample chamber, said reference chamber and said zero calibration channel.

65. An isotopic gas analyzer according to claim 1 and wherein said sample chambers are interconnected pneumatically.

66. An isotopic gas analyzer according to claim 1 and wherein said reference chambers are interconnected pneumatically.

67. An isotopic gas analyzer according to claim 1 and wherein said sample chambers are connected thermally.

68. An isotopic gas analyzer according to claim 1 and wherein said reference chambers are connected thermally.

69. An isotopic gas analyzer according to claim 1 and wherein said first and said second isotopic components of said gas have a region of spectral overlap, and also comprising a system for lowering the pressure of said sample of gas, such that an absorption measurement in said region of spectral overlap is performed under conditions of lowered sample gas pressure.

* * * * *